(12) United States Patent
Feng et al.

(10) Patent No.: US 8,765,908 B2
(45) Date of Patent: Jul. 1, 2014

(54) COMPOSITIONS FOR IMPROVING BONE MASS

(75) Inventors: Xu Feng, Birmingham, AL (US); Shunqing Wang, Guangzhou (CN)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/571,489

(22) Filed: Aug. 10, 2012

(65) Prior Publication Data

US 2013/0012445 A1    Jan. 10, 2013

Related U.S. Application Data

(63) Continuation of application No. PCT/US2011/024347, filed on Feb. 10, 2011.

(60) Provisional application No. 61/302,979, filed on Feb. 10, 2010.

(51) Int. Cl.
*C07K 14/51* (2006.01)
*A61K 38/17* (2006.01)

(52) U.S. Cl.
USPC ............................ 530/324; 514/16.7; 514/18.9

(58) Field of Classification Search
None
See application file for complete search history.

(56) References Cited

U.S. PATENT DOCUMENTS

| | | | |
|---|---|---|---|
| 7,317,096 B1 * | 1/2008 | Noteborn et al. | 536/23.1 |
| 2003/0109444 A1 | 6/2003 | Lam et al. | |
| 2005/0255114 A1 * | 11/2005 | Labat et al. | 424/146.1 |
| 2007/0191279 A1 | 8/2007 | Cronstein et al. | |
| 2008/0305501 A1 | 12/2008 | Feng et al. | |
| 2009/0035315 A1 | 2/2009 | Christgau et al. | |

FOREIGN PATENT DOCUMENTS

WO    WO 01/79449 A2 * 10/2001

OTHER PUBLICATIONS

Bowie et al. Deciphering the message in protein sequences: tolerance to amino acid substitutions. Science, (Mar. 16, 1990) 247 (4948) 1306-10.*
Ngo et al., In The Protein Folding Problem and Tertiary Structure Prediction, Merz and Le Grand (Eds), Aug. 1994, Springer Verlag, pp. 433 and 492-495.*
International Search Report for PCT Application No. PCT/US2011/024347 mailed Dec. 9, 2011 (6 pages).

* cited by examiner

*Primary Examiner* — David Romeo
(74) *Attorney, Agent, or Firm* — Sutherland Asbill & Brennan LLP

(57) ABSTRACT

The present invention provides a therapeutic composition, and method of use thereof, for improving bone mass, rigidity, or strength, or preventing and treating bone loss via modulation of the RANK signaling pathway. The therapeutic composition of the present invention comprises a RYBP peptide, or fragments thereof, that specifically interact with a motif of RANK to regulate osteoclastogenesis. The present invention further provides a composition, and method of use thereof, comprising a modulator that is capable of modulating the RYBP-RANK interaction, or modulating an effector in the RANK signaling pathway through the RYBP-RANK interaction.

10 Claims, 15 Drawing Sheets

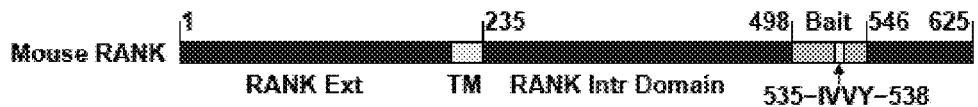
FIGURE 1A
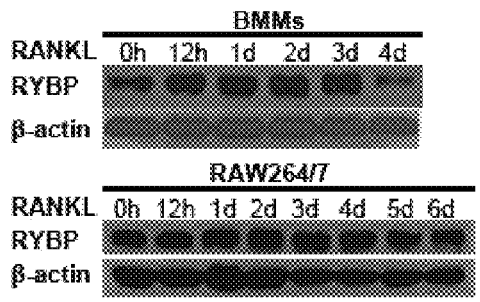
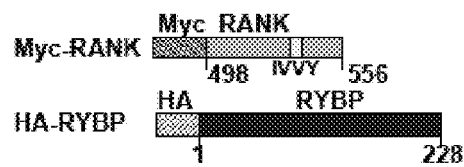
FIGURE 1B
FIGURE 1C
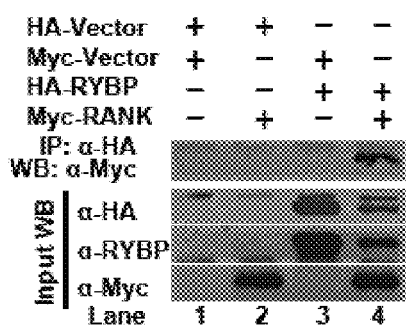
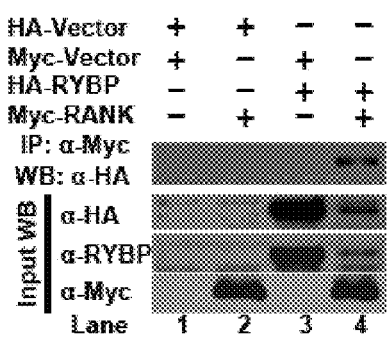
FIGURE 1D
FIGURE 1E
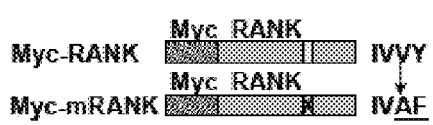
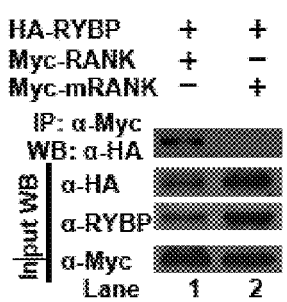
FIGURE 1F
FIGURE 1G

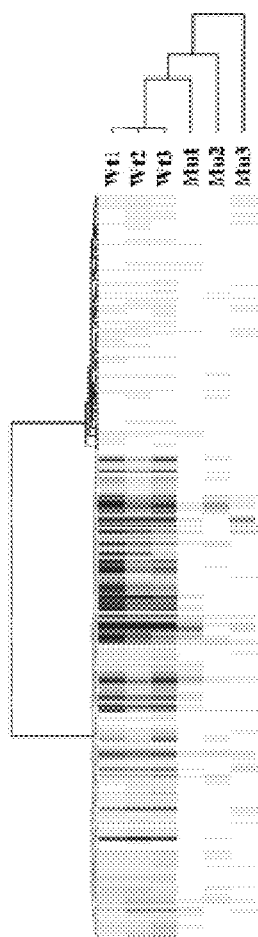
FIGURE 5A
|  | p<0.05 | p<0.02 | p<0.01 | p<0.005 |
|---|---|---|---|---|
| FC>1.1 | 203 | 79 | 41 | 23 |
| FC>1.5 | 72 | 36 | 21 | 9 |
| FC>2.0 | 49 | 26 | 16 | 9 |
| FC>3.0 | 36 | 20 | 12 | 6 |
FIGURE 5B
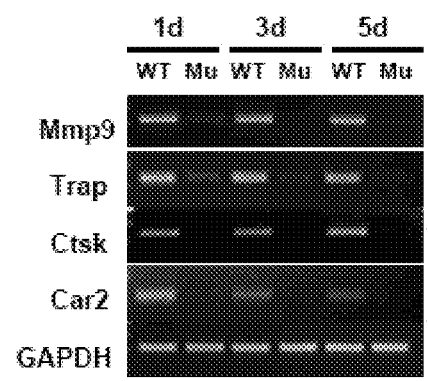
FIGURE 5C

```
234 CYRKKGKALTANLWHWINEACGRLSGDKESSGDSCVSTHTANFGQQGACESVLLLTLEEK hRANK
    |||  ||||||||| |   ||  ||| |||||    ||    |    || ||| || |||
235 YYRKGGKALTANLWNWVNDACSSLSGNKESSGDRCAGSHSATSSQQEVCEGILLMTREEK mRANK

294 TEEEDNCYPDQGGVCQGTCVGGGPYAQGEDARMLSLVEKTEIEEDSFRQMPTEDSYMDRP hRANK
    ||     |  |||  |   ||| |    |   | ||| |   |    ||   |||:|| |||
295 MVEE-----DGAGVCGPVCAAGGPWAEVRDSRIFTLVSEVETQGDLSEKIPTEDSYTDRP mRANK

354 SQETDQLLFLTEPGSKSTEPFSEELEVGENDSLSQCETGTQSTVGSESCNCTEPLCRTDW hRANK
    ||||   | |  ||||||| |||||||||||||||||||| |||| ||   ||  |||
350 SQESTGSLLLIQQGSKSIEPFQEELEVGENDSLSQCETGTESTVDSEGCDSTEPPSRTDS mRANK
                         └─────┘

414 TPMSSENYLQKEVDSGHCPHKAASSSINWADVCTGCRNEPGEDCEPLVGSPKRGPLPQCA hRANK
    |   |   |     |    |      |   |    ||  |||| | |||  |||||||
410 MPVSPEKHLTKEIEGDSCLPWVV--SSNSTDGYTGSGNTPGEDHEPFSGSLKCGPLPQCA mRANK

474 YGMGLPEEEEASRTEARDQPEDGADGRLESSARAGAGSGSSPGGQSPASGNVTGNSMSTF hRANK
    |  |  || ||| || || |   |||| |       ||||||||||||||||||||||
468 YSMGFPSEAAASMAEAGVRPQDRABE------RGASGSGSSPSDQPPASGNVTGNSMSTF mRANK

▬▬▬▬
534 ISSGQVMNFKGDIIVVYVSQTSQEGAAAA---AEPMGSPVQEETLARRDSEAGNGSREPD hRANK
    ||||||||||||||||||||||||||       |  | |||||||| |||  |  ||||
522 ISSGQVMNFKGDIIVVYVSQTSQEGPGSAEPESEPVGSPVQEETLAHRDSEAGTASREPD mRANK
        Bait                          └─────┘

591 PCGGPEGL------REPEKASEPVQEQQGAKA 616 hRANK
    |   ||       |      | |||||  ||
582 VCATGAGLQEDGAPROKDGTSEPVQEQQGAQTSLHTQGSGQCAE 625 mRANK
                         └─────┘
```

FIGURE 6

```
       gcggcggcgc gcgcagctgt ggggcgccgg gggccagccc gtccATGacc atgggcgaca
                                                    1 M   T   M  G  D    D1 agaagagccc gaccaggcca aaaagacaag cgaaacctgc cgcagacgaa ggctttgggg
  6  K  K  S   P  T  R  P   K  R  Q    A  K  P    A  D  E    G  F  W     D2 attgtagcgt ctgcaccttt aggaacagcg ccgaagcctt taaatgcagc atctgcgatg
 26  D  C  S   V  C  T  F   R  N  S    A  E  A    F  K  C  S  I  C  D    D3 tgcggaaagg cacctccacc aggaaacctc gcatcaattc tcagctggtg cacagcagg
 46  V  R  K   G  T  S  T   R  K  P    R  I  N  S  Q  L  V   A  Q  Q     D4 tggcacagca gtacgccact ccacctcccc ctaagaagga gaagaaggag aaggtcgaaa
 66  V  A  Q   Q  Y  A  T   P  P  P    P  K  K  E  K  K  E   K  V  E     D5 agcctgacaa agaaaagcca gagaaagaca aggacattag ccccagtgtc accaagaaaa
 86  K  P  D   K  E  K  P   E  K  D    K  D  I  S  P  S  V   T  K  K     D6 acaccaacaa gaaaacaaaa ccaaagtctg atattctgaa agatcctcct agtgaagcta
106  N  T  N   K  K  T  K   P  K  S    D  I  L  K  D  P  P   S  E  A     D7 acagcataca gtctgctaac gctacaacaa agaccagcga aacaaaccac acctaaggc
126  N  S  I   Q  S  A  N   A  T  T    K  T  S  E  T  N  H   T  R  R     D8 cccggctgaa gaatgtggac aggagcaccg cacagcagtt ggcagtaact gtgggcaacg
146  P  R  L   K  N  V  D   R  S  T    A  Q  Q  L  A  V  T   V  G  N     D9 tcaccgtcat tatcacagac tttaaggaaa agactcgctc ctcctccaca tcctcttcca
166  V  T  V   I  I  T  D   F  K  E    K  T  R  S  S  S  T   S  S  S     D10 cagtgacctc cagtgcaggg tcagaacaga agaaccagag cagctcgggc tcagagagca
186  T  V  T   S  S  A  G   S  E  Q    Q  N  Q  S  S  S  G   S  E  S     D11 cagacaaagg ctcctcccgc tcctccacgc caaagggcga catgtcagca gtgaatgatg
206  T  D  K   G  S  S  R   S  S  T    P  K  G  D  M  S  A   V  N  D aatctttcTG Agattgcaca tggaattgtg aaactatgaa tcagggtatg agattcaaac
226  E  S  F
```

```
1981 accaatgcagttgttagtcttttcttcttaaaacctactatggctcatttattaaacaag
2041 ggttgtcaacctcacatccagacctgacacagagatcttccagtctctggagtcagttct
2101 tagttccttgtgtgggaaaggatcgcaggggtgcatgggcgagttgcgggaaagctcac 2161 ttcccaggagagtgaatgaatagtaggtgttctttgttgactgaactcttgaaagcttt
2221 catttcaccatttaggggtaggagataatgaaagaccactgataatagtttatcatcc
2281 catcccaagtctcagtgactctgctttgctcttagattcagggtatctctcctatctgac
2341 ttagcttcatgtccaccgagtttgtagtgcttaagtcacattaagcatgtggtgttaacc
2401 ttcctttagtttatcacactcaaggactcataggagagcgtgtaagggaacaccgactct
2461 tggtggtaaaagaaccgggtttgcttaataaaagaatttctatgtgtggagcgaacaagt
2521 taagaacatattaacagcttgaattgagtagccaacaggaatggttccattcacatttac
2581 attaaaaccagtcattcgatgcgcggagtctgtccacaaaggcagtgctatttgtcaat
2641 gggctcctgttctcgacgcatggacaatgctcccctcttttaaaacagtgcttgtgtct
2701 gggatgcaagctgtacttaccttttaaataccttttaaagtatttattaatgaaccaa
2761 aggaaaccaggtgctttctgtaagcatcagaatatataatacatagtgatttgactatga
2821 attttaaatccacattttaatattagtgggtattgcaaagacattccttctaaagtttt
2881 aatattcctttattaaggggtctcagggagggttaattagtcagccatatttatttcca
2941 gaggtgtaaggaattgctaagttttttaattaacttttaaaaaaaaaattaaatgccac
3001 caaattcatgtggattgcactgctctttgaaccaatagtgttggtatgcacttttgttca
3061 gaaacactgtgtactttttcaaaacgagtttcatgtaaagtgattggaccccctagatta
3121 gtggaaaaggctgatttaccagctcctcataggctactaattcattcatcgctggtgtct
3181 tgggttttcagttttgcctccatgataaattaaagaatgaggagaggtgaaggagggaa
3241 ggaccacttcagaactagtgaacttgccttgaggtagaaactgcagtggtggagtctaag
3301 cagtcagatgttcctggccgccctgtctcggctgtcgtgggctgcgttgggatagagagg
3361 tgataggtgccacacaatgccatcctcaggcatgcattctggaaatggaattcctattag
3421 cttcctgcatttacagtttgccctgctatagtactccgtaggtaaaaacactagtgtagc
3481 ttacaaagagacattaagaggaccagaaatacttggttattcagtggcacagaaagaaagc
3541 agattaaaacaaaaagcacagtgttaaggcttgcaagtttcccgtgcgtttagtacatga
3601 tctttcacactcgtgtgcacacacacagctgagctgacatgctctgcccgagtcatgcag
3661 ttgggaaggggaaaagacatcttgacacccacgagaatatttaatcaaaaccttcag
3721 tttggatctggatacttcaaaacattggcagacgcttctgtgagtttagctccactaaga
3781 tgtctcgctgcctattaagaccattctcagtctacatttttaagctgccgtatcttaa
3841 attattgagaatttattaattgctgactatataataacctttgcttgtatgttacggaaa
3901 atggtttaagagccaacatttagagtgtgacaatggagctgaacagtttctaacgcgcaa
3961 gcagttctgttcttgtgtatgacttgtaaccttaatttactgtgtaaagatggttacatt
4021 atttccttagctttgtttgttggagacagatagcgaatgcttgttaagtatgtcaacata
4081 atctcccttgtgaacttttgttaatgtcttatacgagctctcttttccatttgcccaga
4141 aaggtggcttgtataacgctttggaagtttctgctccgtccgtcttagagctgacagtct
4201 gttaggtttgttttctcttcatgctaaagtgtcggtggttttgtgaactggtcagaaatt
4261 cacaggtcttaaatgtttggggaaatttatattggacactgctctttgtctagcaaata
4321 aaagatgttaatatattcctgttattggcatgtgcacgactgttattagaagccacttta
4381 tcattttcctgctttaaatagaaatgtctatttatgaattctgcttgtagttttttcaca
4441 aataaaatagtaaatttaaaaaaaaaaaaa
```

FIGURE 8
(Continued)

COMPOSITIONS FOR IMPROVING BONE MASS

CROSS-REFERENCE TO RELATED APPLICATIONS

This patent application is a continuation of PCT Application No. PCT/US2011/024347, filed Feb. 10, 2011, which claims priority benefit of U.S. Provisional Application No. 61/302,979 filed Feb. 10, 2010, each of which is incorporated herein by reference in their entireties.

GOVERNMENT SUPPORT STATEMENT

This invention was made with government support under Grant No. AR47830 awarded by National Institute of Arthritis and Musculoskeletal and Skin Diseases (NIAMS). The government has certain rights in the invention.

FIELD OF THE INVENTION

The present invention relates to the compositions and methods for improving bone mass, rigidity, or strength, or preventing and treating bone loss via RANK signaling pathway.

BACKGROUND OF THE INVENTION

Osteoclasts, the sole bone-resorbing cell, not only play a pivotal role in skeletal development and maintenance but are also implicated in the pathogenesis of various bone disorders including postmenopausal osteoporosis and tumor bone metastasis (Teitelbaum, 2000; Raisz, 2005; Mundy, 2002). Osteoclasts are multinucleated giant cells that differentiate from mononuclear cells of the monocyte/macrophage lineage (Teitelbaum, 2000), thus involving both dramatic phenotypic changes and reprogramming of gene expression. Osteoclastogenesis requires two essential factors: the monocyte/macrophage-colony stimulating factor (M-CSF) and the receptor activator of NF-κB ligand (RANKL) (Suda et al., 1999; Teitelbaum, 2000; Boyle et al., 2003).

RANKL (also known as OPGL, ODF and TRANCE), a member of the tumor necrosis factor (TNF) family, was discovered independently by several groups (Anderson et al., 1997; Wong et al., 1997b; Lacey et al., 1998; Yasuda et al., 1998) in the late 1990s and thus far has been shown to regulate diverse physiological processes such as bone remodeling (Lacey et al., 1998; Yasuda et al., 1998), dendritic cell (DC) survival and activation (Wong et al., 1997a; Josien et al., 1999; Josien et al., 2000), T-cell activation (Kong et al., 1999; Bachmann et al., 1999), lymph node organogenesis (Kong et al., 1999; Dougall et al., 1999; Kim et al., 2000a), B-cell differentiation (Kong et al., 1999; Dougall et al., 1999), mammary gland development (Fata et al., 2000), and thermoregulation in females or fever response inflammation (Hanada et al., 2009). RANKL regulates various biological functions by binding to and activating its receptor RANK (Hsu et al., 1999), which belongs to the TNF receptor (TNFR) family (Anderson et al., 1997). RANKL also has a decoy receptor, osteoprotegerin (OPG) (Simonet et al., 1997; Tsuda et al., 1997), which inhibits RANKL function by competing with RANK for binding RANKL (Yasuda et al., 1998; Lacey et al., 1998).

In bone, RANKL and RANK play important roles in osteoclastogenesis: Mice lacking either protein develop osteopetrosis due to failure to form osteoclasts (Kong et al., 1999; Dougall et al., 1999; Li et al., 2000; Kim et al., 2000b). Consistently, mice deficient for OPG develop early onset of osteoporosis due to elevated osteoclastogenesis (Bucay et al., 1998; Mizuno et al., 1998) whereas transgenic mice overexpressing OPG exhibit osteopetrosis, resulting from a decrease in late stages of osteoclastogenesis (Simonet et al., 1997).

The discovery of the RANKL/RANK/OPG axis was soon followed by an intensive investigation of RANK-activated intracellular signaling pathways involved in the regulation of the diverse functions. The initial efforts primarily focused on TNF receptor associated factor (TRAF)-dependent pathways since RANK was identified as a member of the TNF receptor (TNFR) family (Anderson et al., 1997) and members of the TNFR family, which lack intrinsic enzymatic activity, transduce intracellular signals by recruiting various TRAFs via specific motifs in the cytoplasmic domain (Locksley et al., 2001; Chung et al., 2002). Numerous biochemical and functional studies have established that RANK contains three functional TRAF-binding sites (PFQEP (SEQ ID NO: 11) 369-373, PVQEET (SEQ ID NO: 12) 559-564 and PVQEQG (SEQ ID NO: 13) 604-609) that redundantly play a role in osteoclast formation and function (Liu et al., 2004) (Liu et al., 2005; Hsu et al., 1999; Darnay et al., 1998; Wong et al., 1998; Kim et al., 1999; Darnay et al., 1999; Galibert et al., 1998). Collectively, through these functional TRAF-binding motifs, RANK activates six major signaling pathways NF-κB, JNK, ERK, p38, NFATc1 and Akt, which play important roles in osteoclast formation, function and/or survival (Boyle et al., 2003; Liu et al., 2004; Feng, 2005).

On the other hand, several lines of evidence support that RANK may also activate a TRAF-independent signaling pathway(s) essential for osteoclastogenesis. It has been shown that TRAF6 acts as a key downstream signaling molecule for both RANK and IL-1R (Wu and Arron, 2003) and a single TRAF6-binding motif is able to promote osteoclastogenesis (Ye et al., 2002; Liu et al., 2004). However, administration of IL-1 to RANK−/− mice failed to induce any osteoclastogenesis in vivo (Li et al., 2000), indicating that an unidentified TRAF6-independent signaling pathway(s) is also required for osteoclastogenesis. Moreover, consistent with this in vivo finding, in vitro studies also demonstrated that IL-1 failed to stimulate osteoclastogenesis (Azuma et al., 2000; Kobayashi et al., 2000). Given that the TRAF independent signaling pathway(s) is most likely initiated by one or more motifs in the RANK cytoplasmic domain, a systematic structure/function study of the RANK cytoplasmic domain was carried out using a chimeric receptor approach (Xu et al., 2006). This study has led to an identification of a specific 4-a.a. RANK motif (IVVY (SEQ ID NO: 4) 535-538), which shares no homology with any of the known TRAF-binding sites but plays a crucial role in osteoclastogenesis by committing bone marrow macrophages (BMMs) to the osteoclast lineage (Xu et al., 2006). However, the precise molecular mechanism by which this RANK motif mediates the lineage commitment remains elusive.

RYBP (Ring1A and YY1 binding protein, also known as DEDAF and YEAF1, Genbank Accession No. BC080287) was initially identified as a protein interacting with the Polycomb group (PcG) proteins, Ring1A and M33, and the transcriptional factor YY1 in a two-hybrid screen and shown to mediate transcriptional repression in reporter assays (Garcia et al., 1999). It was later shown that RYBP also interacts with several members of the E2F family of transcription factors (Trimarchi et al., 2001; Schlisio et al., 2002), the transcriptional factor E4TF1/hGABP (Sawa et al., 2002) and ubiquitinated H2A (Arrigoni et al., 2006), a Ring1A/Ring1B-dependent chromatin mark associated with transcriptional repression (Li et al., 2007). RYBP knockout mice exhibited embryonic lethality, revealing its essential role in development (Pirity et al., 2005). In addition to embryonic lethality, either loss- or gain-of-function experiments revealed other developmental alterations including defects in neural tube closure and formation of anterior eye structures (Pirity et al., 2005; Gonzalez et al., 2008). Intriguingly, RYBP was also identified in an independent two-hybrid screen as a protein interacting with death effector domain (DED)-containing proteins such as FADD, procaspase 8, and procaspase 10 and thus named differently as the death effector domain-associated factor (DEDAF) (Zheng et al., 2001). Moreover, RYBP has other interacting partners with roles in apoptosis, the viral apoptin protein and Hippi (Danen-van Oorschot et al., 2004; Stanton et al., 2007). Consistent with a proapoptotic function for RYBP, over-expression of RYBP in cell lines promote apoptosis (Zheng et al., 2001; Danen-van Oorschot et al., 2004). A recent study has revealed that RYBP interacts with MDM2 to alter the MDM2-p53 interaction, resulting in stabilization of p53, and thus may act as a tumor suppressor (Chen et al., 2009).

PcG proteins were originally identified in Drosophila as repressors of Hox genes, a family of transcription factors that control the anteroposterior segmentation of the fruitfly body (Schuettengruber et al., 2007). Homologues of Drosophila PcG proteins have subsequently been identified in vertebrates and plants and shown to be implicated in cell differentiation, stem cell identity, tumorigenesis and genomic imprinting (Schwartz and Pirrotta, 2008; Schwartz and Pirrotta, 2007; Kohler and Villar, 2008). PcG proteins form three major PcG complexes termed Polycomb repressive complexes (PRC) 1, PRC2 and PhoRC. The core components of the PRC1 complex include mammalian homologues of Drosophila Polycomb (PC), Posterior Sex Combs (PSC), Polyhomeotic (PH), and dRING. Specifically, RYBP interacts with Ring1A and Ring1B, two mammalian homologues of dRING, and M33 (also known as CBX2), a mammalian homologue of PC (Garcia et al., 1999; Gecz et al., 1995). The PRC2 complex primarily includes mammalian homologues of the E(Z) H3K27 methyltransferase, SU(Z)12, and Extra sex combs (ESC). PhoRC contains the mammalian transcription factor YY1, homologous to Drosophila Pleiohomeotic (PHO). The PRC2 complex is responsible for catalyzing the tri-methylation of lysine 27 on histone 3 (histone H3K27me3) in the PcG target genes, which is recognized by the PRC1 complex through the mammalian homologues of Drosophila PC (Cao and Zhang, 2004). Despite the ability of RYBP to associate with PcG proteins, the functional significance of the interaction in the regulation of PcG target genes is still unknown.

SUMMARY OF THE INVENTION

The present invention provides a therapeutic composition for improving bone mass, rigidity, or strength, or preventing or treating bone loss caused by bone diseases, such as osteoporosis, bone erosion in rheumatoid arthritis, periodontal bone loss, and tumor (e.g., breast, prostate and multiple myeloma)-induced osteolysis (bone destruction) and bone metastasis, or other pathological conditions involving elevated osteoclast formation/activity, such as Paget disease and drug-induced bone loss. Such therapeutic composition comprises a therapeutically acceptable excipient and a peptide, or a fragment thereof, that specifically binds to a RANK fragment containing an IVVY (SEQ ID NO:4) motif so as to regulate osteoclastogenesis. In certain embodiments, the peptide derived from a portion or all of RYBP protein a protein interacting with components of the polycomb group (PcG) complexes (and also referred to by its accession number BC080287 in Genbank) is a RING1A and YY1 binding protein, encoded by a nucleic acid sequence as set forth in SEQ ID NO:1, and having at least a portion of the deduced amino acid sequence as set forth in SEQ ID NO:2 (FIG. 8), or an analog thereof.

In certain embodiments, the fragment of the peptide comprises an amino acid sequence SRPRLKN-VDRSTAQQLAVTVGNVTVIITDFKEKTRSSSTS (SEQ ID NO:3), or an analog or further fragment thereof, that specifically interacts with the IVVY (SEQ ID NO:4) motif of RANK. In certain embodiments, the fragment of the peptide comprises at least the four amino acid sequence VIIT (SEQ ID NO:5) or AVTV (SEQ ID NO:6), or an analog thereof, that specifically interacts with the IVVY (SEQ ID NO:4) motif of RANK.

The present invention further provides a method of improving bone mass, rigidity, or strength, or preventing or treating bone loss caused by bone diseases, such as osteoporosis, bone erosion in rheumatoid arthritis, periodontal bone loss, and tumor (e.g., breast, prostate and multiple myeloma)-induced osteolysis (bone destruction) and bone metastasis, or other pathological conditions involving elevated osteoclast formation/activity, such as Paget disease and drug-induced bone loss, comprising administering to a subject in need an effective amount of a therapeutic composition comprising a therapeutically acceptable excipient and RYBP, or a fragment thereof, that specifically interacts with the IVVY (SEQ ID NO:4) motif of RANK. In certain embodiments, the RYBP protein comprises the amino acid sequence as set forth in SEQ ID NO:2 (FIG. 8), or an analog thereof. In certain embodiments, the fragment of RYBP comprises an amino acid sequence as set forth in SEQ ID NO:3, or an analog or functional fragment thereof, that specifically interacts with the IVVY (SEQ ID NO:4) motif of RANK. In certain embodiments, the fragment of RYBP comprises at least the four amino acid sequence VIIT (SEQ ID NO:5) or AVTV (SEQ ID NO:6), or a natural or synthetic analog thereof, that specifically interacts with the IVVY (SEQ ID NO:4) motif of RANK.

The present invention also provides a therapeutic composition, or a method of regulating osteoclastogenesis thereof, comprising a small molecule, peptide, protein, drug, naturally-occurring, or chemically synthesized, known or later discovered, that is capable of modulating an interaction of RYBP, or a fragment thereof, with the IVVY (SEQ ID NO:4) motif of RANK, or modulating any downstream effectors in the RANK signaling pathway through the interaction of RYBP, or a fragment thereof, with the IVVY (SEQ ID NO:4) motif of RANK. The present invention provides that the IVVY (SEQ ID NO:4) motif of RANK engages RYBP, or a fragment thereof, to regulate osteoclastogenesis. The present invention provides that RYBP, or a fragment thereof, is a high affinity IVVY (SEQ ID NO:4) motif-binding protein functionally involved in osteoclastogenesis. RYBP is predominantly present in nuclei of osteoclast precursors. RANKL induces nucleocytoplasmic shuttling of RYBP in an IVVY (SEQ ID NO:4) motif dependent manner, leading to the activation of osteoclast genes. Therefore, RYBP, or a fragment thereof, is an important protein engaged in transmitting the IVVY (SEQ ID NO:4)-activated membrane-proximal signals to a mammalian cell nucleus to promote osteoclastogenesis via control of the expression of about 200 genes, including, but not limited to, osteoclast-related genes such as matrix metallopeptidase 9 (Mmp9), cathepsin K (Ctsk) and tartrate resistant acid phosphatase 5 (TRAP). Any drug, modulator, protein, peptide, small molecule, nucleic acid, siRNA, or oligonucleotide that is capable of modulating these gene or protein expressions via RYBP-RANK signalling is also within the scope of the present invention.

BRIEF DESCRIPTION OF THE DRAWINGS

FIG. 1 illustrates that RYBP interacts with the RANK IVVY (SEQ ID NO:4) Motif. (A) Schematic location of the RANK region used as bait in the two-hybrid screen. The mouse RANK is 625-a.a. long. The bait corresponds to a 59-a.a. RANK cytoplasmic region (a.a. 498-556) which is highly conserved in a.a. sequence between the mouse and human and contains the IVVY (SEQ ID NO:4) (535-538) motif (Bejarano et al., 2005, FIG. 1 on page 1120 showing there are only two differences at residues 86 and 96 in the 226 a.a. RYBP protein and the two differences are located outside of the interacting region). TM: transmembrane domain; Ext: extracellular domain; Intr: intracellular domain. (B) Expression of RYBP during osteoclast differentiation. Primary BMMs were treated with MCSF (44 ng/ml) and RANKL (100 ng/ml) while macrophage-like RAW264.7 cells were stimulated RANKL (100 ng/ml) alone to promote osteoclast formation. Cells were lysed at various time points for assessment of RYBP expression by Western blots with anti-RYBP antibody (α-RYBP). Loading control was performed with anti-β-actin antibody (β-actin). (C) Schematic structure of Myc-RANK and HA-RYBP. FIG. 1C discloses "IVVY" as SEQ ID NO: 4. (D) RANK fragment 498-556 interacts with RYBP in mammalian cells. Myc-RANK, HA-RYBP and the two corresponding empty vectors (Myc-Vector and HA-Vector) were transiently transfected in different combinations into 293T cells. Cells were then lysed for co-immunoprecipitation assays (Co-IP) in which immunoprecipitation (IP) was performed with anti-HA antibody (α-HA), followed by Western blots (WB) with anti-Myc antibody (α-Myc) to assess the interaction between the RANK region and RYBP. The expression levels of the tagged proteins in transfected cells were determined by input WB with α-HA, a-RYBP and a-Myc. (E) The interaction between RANK fragment 498-556 and RYBP was further demonstrated by performing reverse Co-IP assays, in which IP was performed with α-HA, followed by WB with α-Myc. (F) Myc-mRANK differs from Myc-RANK in that it contains inactivating mutations in the IVVY (SEQ ID NO:4) motif (IVVY (SEQ ID NO:4)→IVAF (SEQ ID NO:7)). (G) The IVVY (SEQ ID NO:4) motif is specifically responsible for the interaction between RANK fragment 498-556 and RYBP. HA-RYBP was co-transfected with Myc-RANK or Myc-mRANK into 293T cells. IP was performed with α-Myc, followed by WB with α-HA. Input WB assays were performed as in (D).

FIG. 6 illustrates sequence and location of RANK cDNA region encoding the bait for two-hybrid screening. Human and mouse RANK cytoplasmic domains are shown and compared. The three boxed sequences are functional TRAF-binding sites. The IVVY (SEQ ID NO:4) motif that is essential for osteoclastogenesis is indicated by a black bar on top of the sequence. The 49-aa segment containing the IVVY (SEQ ID NO:4) motif, which is used as bait for two-hybrid screen, is shown in bold and underlined. hRANK: human RANK (SEQ ID NO: 27); mRANK: mouse RANK (SEQ ID NO: 28).

FIG. 7 illustrates amino acid sequence and location of regions deleted in D1-D11. Both mouse RYBP amino acid sequence (SEQ ID NO: 2) and corresponding coding sequence (SEQ ID NO: 29) are shown. Numbers on left indicate the location of the amino acid residues. The deleted region in each mutant is specified d by vertical lines. The specific residues deleted in these mutants are: residues 4-23 in D1; residues 24-43 in D2; residues 44-63 in D3; residues 64-83 in D4; residues 84-103 in D5; residues 104-123 in D6; residues 124-143 in D7; residues 144-163 in D8; residues 164-183 in D9; residues 184-203 in D10; residues 204-228 in D11.

FIG. 8 illustrates/underlined location and sequence of effective siRNA target in full length mouse RYBP cDNA, of SEQ ID NO:1 and deduced amino acid sequence of SEQ ID NO:2.

DETAILED DESCRIPTION OF THE INVENTION

Figure 2A:
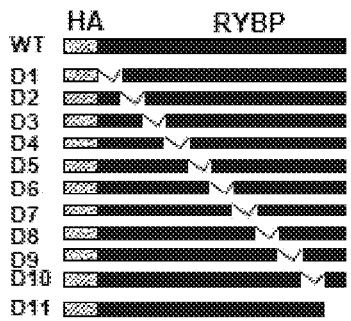
FIG. 2 provides identification of specific RYBP domains interacting with the RANK IVVY (SEQ ID NO:4) motif. (A) Schematic diagram of 11 deletion mutants (D1-D11) of HA-RYBP (WT). In each mutant construct, a region of around 20-aa was deleted. (B) Myc-RANK was co-transfected with HA-tagged WT or one mutant RYBP construct (HAConst) as shown in left panel into 293T cells. IP was performed with α-Myc, followed by WB with α-HA. Input WB assays were performed as in FIG. 1D. (C) Top illustration depicts schematic location of the 40-a.a. RYBP region (deleted in D8 and D9) which was shown to be required for interacting with the RANK IVVY (SEQ ID NO:4) motif in (A). Bottom panel shows the sequence of the 40-a.a. region (SEQ ID NO: 3) and schematic structure of 10 deletion mutants (S1-S10) (SEQ ID NOS14-23, respectively, in order of appearance), each with 4 amino acid residues within the 40-a.a. region deleted. (D) Co-IP assays in (A) were repeated with S1-S10. (E) Location and sequence of two RYBP domains (SEQ ID NOS 24 and 3, respectively, in order of appearance) mediating the interaction with the RANK IVVY (SEQ ID NO:4) motif. Ext: extracellular domain; Intr: intracellular domain.

The present invention provides a pharmaceutically administerable therapeutic composition, and method of use thereof, for promoting, or inhibiting, RANK signalling required for osteoclast formation, function and/or survival. The compositions and methods can be used for improving bone mass, rigidity, or strength, or preventing or treating bone loss caused by bone diseases, such as osteoporosis, bone erosion in rheumatoid arthritis, periodontal bone loss, and tumor (e.g., breast, prostate and multiple myeloma)-induced osteolysis (bone destruction) and bone metastasis, or other pathological conditions involving elevated osteoclast formation/activity, such as Paget disease and drug-induced bone loss. Such therapeutic composition comprises a therapeutically acceptable excipient and a peptide, or a fragment thereof, that specifically binds to a RANK fragment containing a IVVY (SEQ ID NO:4) motif so as to regulate osteoclastogenesis.

In certain embodiments, the peptide is RYBP protein having an amino acid sequence as set forth in SEQ ID NO:2, or fragments or analogs thereof. In certain embodiments, the fragment of the peptide has, consists of, or comprises an amino acid sequence SRPRLKNVDRSTAQQLAVTVGN-VTVIITDFKEKTRSSSTS (SEQ ID NO:3), or fragments or analogs thereof, that specifically interacts with the IVVY (SEQ ID NO:4) motif of RANK. In certain embodiments, the fragment of the peptide has, consists of, or comprises at least the four amino acid sequence VIIT (SEQ ID NO:5) or AVTV (SEQ ID NO:6), or homologs or analogs thereof, that specifically interacts with the IVVY (SEQ ID NO:4) motif of RANK.

The present invention also provides a therapeutic composition, or a method of regulating osteoclastogenesis thereof, comprising a small molecule, peptide, protein, drug, naturally-occurring, or chemically synthesized, known or later discovered, that is capable of modulating an interaction of RYBP, or a fragment thereof, with the IVVY (SEQ ID NO:4) motif of RANK, or modulating any downstream effectors in the RANK signaling pathway through the interaction of RYBP, or a fragment thereof, with the IVVY (SEQ ID NO:4) motif of RANK. The invention further provides a valuable research tool for screening and identifying additional molecules which modulate the interaction of RYBP, or a fragment thereof such as provided in SEQ ID NOS: 5 and 6, with the RANK motif IVVY (SEQ ID NO:4).

The present invention also provides isolated nucleotides, homologs and analogs that encode RYBP, or portions thereof, as set forth in SEQ ID NO:2, SEQ ID NO:3; SEQ ID NO:5, or SEQ ID NO:6; or hybridize at highly stringent conditions to the nucleotide sequence encoding the amino acid sequence as shown in SEQ ID NO:2, SEQ ID NO:3, SEQ ID NO:5, SEQ ID NO:6, or portions thereof. Moreover, the present invention provides nucleotides, homologs and analogs that comprise the nucleotide sequences encoding the amino acid sequence shown in SEQ ID NO:2, SEQ ID NO:3, SEQ ID NO:5, SEQ ID NO:6, portions, or complements thereof.

As used herein, the sequences of these peptides generally comprise about 3 to about 100 amino acids residues. As used herein, an "amino acid residue" refers to any naturally occurring amino acid, any amino acid derivative or any amino acid mimetic known in the art. Accordingly, the peptides encompass amino acid sequences comprising at least one of the 20 common amino acids found in naturally occurring proteins, or at least one modified or unusual amino acid known in the art or later derived.

The present invention also provides peptide analogs of RYBP, or a fragment thereof. As used herein, the term "analogs" refers to two proteins or peptides that have the same or similar function, but that have evolved separately in unrelated organisms, such as murine and human analogs of the protein referred to herein as RYBP. As used herein, the term "analog" further refers to a structural derivative of a parent compound that often differs from it by a single element. As used herein, the term "analog" also refers to any peptide modifications known to the art, including but are not limited to changing the side chain of one or more amino acids or replacing one or more amino acid with any non-amino acids.

Based on the amino acid sequences of the present invention, any peptides and their analogs comprising such sequences can be made by any techniques known to those of skill in the art, including but are not limited to the recombinant expression through standard molecular biological techniques, the conventional peptide/protein purification and isolation methods, and/or the synthetic chemical synthesis methods. The nucleotide and peptide sequences corresponding to various genes may be found at computerized databases known to those of ordinary skill in the art, for instance, the National Center for Biotechnology Information's Genbank and GenPept databases. Alternatively, various commercial preparations of proteins and peptides are known to those of skill in the art.

Because the length of the peptides of the present invention is relatively short, peptides and analogs comprising the amino acid sequences of these peptide inserts can be chemically synthesized in solution or on a solid support in accordance with conventional techniques. Various automatic synthesizers are commercially available and can be used in accordance with known protocols. Short peptide sequences, usually from about 3 up to about 100 amino acids, can be readily synthesized by such methods. Alternatively, recombinant DNA technology may be employed wherein a nucleotide sequence which encodes a peptide and its analog of the present invention is inserted into an expression vector, transformed or transfected into an appropriate host cell, and cultivated under conditions suitable for expression.

Peptide mimetics may also be used for preparation of the peptides and their analogs of the present invention. Mimetics are peptide-containing molecules that mimic elements of protein secondary structure (Johnson et al., BIOTECHNOLOGY AND PHARMACY, Pezzuto et al., Eds., Chapman and Hall, latest edition, New York). A peptide mimetic is expected to permit molecular interactions similar to the natural molecule, and may be used to engineer second generation molecules having many of the natural properties of the peptides, but with altered and even improved characteristics.

The present invention also provides chimeric or fusion peptides that comprise the amino acid sequences of RYBP, or a fragment thereof, of the present invention, as disclosed herein. As used herein, a "chimeric or fusion peptide" comprises the amino acid sequence corresponding to RYBP (SEQ ID NO:2), or a fragment, e.g., SEQ ID NO:3, SEQ ID NO:5, or SEQ ID NO:6, or analogs thereof, operatively linked, preferably at the N- or C-terminus, to all or a portion of a second peptide or protein. As used herein, "the second peptide or protein" refer to a peptide or protein having an amino acid sequence which is not substantially identical to RYBP, a fragment, or analogs thereof, e.g., a peptide or protein that is different from SEQ ID NO:2, SEQ ID NO:3, SEQ ID NO:5, SEQ ID NO:6, or analogs thereof, and is derived from the same or a different organism. With respect to the fusion peptide, the term "operatively linked" is intended to indicate that the amino acid of RYBP, a fragment, or analogs thereof, and the second peptide or protein are fused to each other so that both sequences fulfill the proposed function attributed to the sequence used.

For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. In certain embodiments, the fusion proteins of the present invention comprise the peptide and/or analog comprising amino acid sequences of RYBP, or a fragment thereof, that is linked to another protein or peptide. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually any protein or peptide could be incorporated into a fusion protein comprising the peptides and analogs of the present invention.

Methods of generating fusion peptides/proteins are well known to those of skill in the art. Such peptides/proteins can be produced, for example, by chemical attachment using bifunctional cross-linking reagents, by de novo synthesis of the complete fusion peptide/protein, or by standard recombinant DNA techniques that involve attachment of a DNA sequence encoding the peptides of present invention, as disclosed herein, to a DNA sequence encoding the second peptide or protein, followed by expression of the intact fusion peptide/protein using. For example, DNA fragments coding for the peptide sequences of RYBP, fragments, or analogs thereof are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers.

Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al., latest edition, John Wiley & Sons). Moreover, many expression vectors are commercially available that already encode a fusion moiety (e.g., a GST polypeptide). The nucleic acids encoding RYBP, fragments, or analogs thereof can be cloned into such an expression vector such that the fusion moiety is linked in-frame to these nucleic acids encoding peptides of RYBP, fragments, or analogs thereof.

In certain embodiments the peptides and analogs of the present invention may be isolated or purified. Protein purification techniques are well known in the art. These techniques involve, at one level, the homogenization and crude fractionation of the cells, tissue or organ to peptide and non-peptide fractions. The peptide/protein of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast protein liquid chromatography (FPLC) or even HPLC.

An isolated peptide is intended to refer to a peptide/protein that is purified to any degree relative to its naturally-occurring state. Therefore, an isolated or purified peptide refers to a peptide free from at least some of the environment in which it may naturally occur. Generally, "purified" will refer to a peptide composition that has been subjected to fractionation to remove various other components, and which composition substantially retains its expressed biological activity. Where the term "substantially purified" is used, this designation will refer to a composition in which the peptide forms the major component of the composition, such as constituting about 50%, about 60%, about 70%, about 80%, about 90%, about 95%, or more of the peptides in the composition.

Various methods for quantifying the degree of purification of the peptide are known in the art. These include, for example, determining the specific activity of an active fraction, or assessing the amount of peptides within a fraction by SDS/PAGE analysis. Various techniques suitable for use in peptide/protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the peptides, fragments, and their analogs always be provided in their most purified state. Indeed, it is contemplated that less substantially purified products will have utility in certain embodiments. Partial purification may be accomplished by using fewer purification steps in combination, or by utilizing different forms of the same general purification scheme. Methods exhibiting a lower degree of relative purification may have advantages in total recovery of protein product, or in maintaining the activity of an expressed protein. The invention contemplates compositions comprising the peptides and a pharmaceutically acceptable carrier or excipients.

In certain embodiments, the RYBP peptide, fragments, and analogs thereof, of the present invention may be attached to imaging agents including but are not limited to fluorescent, and/or radioisotopes including but not limited to $^{125}$I, for imaging, diagnosis and/or therapeutic purposes. Many appropriate imaging agents and radioisotopes are known in the art, as are methods for their attachment to the peptides.

The present invention also provides isolated nucleic acids/nucleotides, homologs and analogs that comprise the nucleotide sequences encoding the RYBP amino acid sequence, fragments, or analogs thereof. As used herein, the "nucleic acids/nucleotides" may be derived from genomic DNA, complementary DNA (cDNA) or synthetic DNA. The term "nucleic acid/nucleotide" also refer to RNA or DNA that is linear or branched, single or double stranded, chemically modified, or a RNA/DNA hybrid thereof. It is contemplated that a nucleic acid within the scope of the present invention may comprise 10-150 or more nucleotide residues in length. Where incorporation into an expression vector is desired, the nucleic acid may also comprise a natural intron or an intron derived from another gene. Less common bases, such as inosine, 5-methylcytosine, 6-methyladenine, hypoxanthine, and others can also be used.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

As used herein, "homologs" are defined herein as two nucleic acids or peptides that have similar, or substantially identical, nucleic acids or amino acid sequences, respectively. The term "homolog" further encompasses nucleic acid molecules that differ from one of the nucleotide sequences due to degeneracy of the genetic code and thus encodes the same amino acid sequences. In one of the preferred embodiments, homologs include allelic variants, orthologs, paralogs, agonists, and antagonists of nucleic acids encoding RYBP (SEQ ID NO:2), fragments, e.g., SEQ ID NO:3, SEQ ID NO:5, or SEQ ID NO:6, or analogs thereof, as defined hereafter.

As stated above, the present invention includes RYBP (SEQ ID NO:2), or fragments (e.g., SEQ ID NO:3, SEQ ID NO:5, or SEQ ID NO:6), and which are intended to include functional equivalents such as homologs and analogs thereof. To determine the percent sequence identity of two amino acid sequences (e.g., one of the sequences of SEQ ID NO: 2, SEQ ID NO:3, SEQ ID NO:5, SEQ ID NO:6, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences.

The percent sequence identity between the two sequences is a function of the number of identical positions shared by the sequences (i.e., percent sequence identity numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence of RYBP (SEQ ID NO:2) or fragments (e.g., SEQ ID NOs:3, 5, or 6). In certain embodiments, the amino acid homologs have sequence identity over at least 1, 2, 3, 4, 5, 6, 7, 8, 9, 10, 20, 30, 40, or more contiguous amino acid residues of the sequence disclosed herein including SEQ ID NO:2, SEQ ID NO:3, SEQ ID NO:5, or SEQ ID NO:6.

In other embodiments, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence encoding amino acid sequences disclosed herein including SEQ ID NO:2, SEQ ID NO:3, SEQ ID NO:5, or SEQ ID NO:6.

The determination of the percent sequence identity between two nucleic acid or peptide sequences is well known in the art. For instance, the Vector NTI 6.0 (PC) software package (InforMax, 7600 Wisconsin Ave., Bethesda, Md. 20814) to determine the percent sequence identity between two nucleic acid or peptide sequences can be used. In this method, a gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the present invention provides an isolated nucleic acid comprising a nucleotide sequence that hybridizes to the nucleotides encoding the amino acid sequence of RYBP (SEQ ID NO:2), fragments (e.g., SEQ ID NOs:3, 5, or 6), homologs, or analogs thereof, respectively under stringent conditions. As used herein with regard to hybridization for DNA to a DNA blot, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in certain embodiments, the phrase "stringent conditions" refers to hybridization in a 6×SSC solution at 65° C. In another embodiment, "highly stringent conditions" refers to hybridization overnight at 65° C. in 10×Denhart's solution, 6×SSC, 0.5% SDS and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, Anal. Biochem. 138:267-284; Current Protocols in Molecular Biology, Chapter 2, Ausubel et al., eds., latest edition, Greene Publishing and Wiley-Interscience, New York; and Tijssen, Laboratory Techniques in Biochemistry and Molecular Biology Hybridization with Nucleic Acid Probes, Part 1, Chapter 2, latest edition, Elsevier, New York.

Using the above-described methods, and others known to those of skill in the art, one of ordinary skill in the art can isolate homologs of RYBP peptide, fragments thereof, comprising amino acid sequence shown in SEQ ID NO:2, SEQ ID NO:3, SEQ ID NO:5, or SEQ ID NO:6. One subset of these homologs are allelic variants. As used herein, the term "allelic variant" refers to a nucleotide sequence containing polymorphisms that lead to changes in the amino acid sequences of RYBP (SEQ ID NO:2) or fragments (e.g., SEQ ID NOs:3, 5, or 6) thereof without altering the functional activities. Such allelic variations can typically result in 1-5% variance in nucleic acids encoding RYBP, or fragments thereof.

In addition, the skilled artisan will further appreciate that changes can be introduced by mutation into a nucleotide sequence that encodes the amino acid sequence of RYBP (SEQ ID NO:2), fragments (e.g., SEQ ID NOs: 3, 5, or 6), or analogs thereof. For example, nucleotide substitutions leading to amino acid substitutions at "non-essential" amino acid residues can be made in a sequence encoding the amino acid sequence of RYBP (SEQ ID NO:2), fragments (e.g., SEQ ID NOs: 3, 5, or 6), or analogs thereof. A "non-essential" amino acid residue is a residue that can be altered without altering the activity of said peptide, whereas an "essential" amino acid residue is required for desired activity of such peptide.

Accordingly, another aspect of the invention pertains to nucleic acid molecules encoding RYBP peptide, fragments or analogs thereof, that contain changes in amino acid residues that are not essential for the peptide activity. In one embodiment, the isolated nucleic acid molecule comprises a nucleotide sequence encoding peptide, wherein the peptide comprises an amino acid sequence at least about 50%, 60-70%, 70-75%, 75-80%, 80-85%, 85-90%, 90-95%, or 95-100% identical to an amino acid sequence, such as the sequence of RYBP (SEQ ID NO:2) or fragments (e.g., SEQ ID NOs: 3, 5, or 6) thereof.

An isolated nucleic acid molecule encoding a peptide having sequence identity with an amino acid sequence of RYBP (SEQ ID NO:2) or fragments (e.g., SEQ ID NOs: 3, 5, or 6) thereof can be created by introducing one or more nucleotide substitutions, additions, or deletions into a nucleotide encoding such peptide sequences, respectively, such that one or more amino acid substitutions, additions, or deletions are introduced into the encoded peptide and/or the side chain of the amino acids constituting the encoded peptides. Mutations can be introduced into the nucleic acid sequence encoding RYBP (SEQ ID NO:2) or fragments (e.g., SEQ ID NOs: 3, 5, or 6) thereof by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in RYBP peptide or fragments thereof is preferably replaced with another amino acid residue from the same side chain family. Alternatively, in another embodiment, mutations can be introduced randomly along all or part of the RYBP peptide sequence or fragments thereof, such as by saturation mutagenesis, and the resultant mutants can be screened for RANK protein interactions. Following mutagenesis of the nucleic acid sequence encoding the RYBP peptide sequence or fragments thereof, the encoded peptide can be expressed recombinantly and the RANK binding activity of the peptide can be determined.

The nucleotides of the present invention may be produced by any means, including genomic preparations, cDNA preparations, in vitro synthesis, RT-PCR, and in vitro or in vivo transcription. It is contemplated that the peptides, their variations and mutations, or fusion peptides/proteins may be encoded by any nucleic acid sequence that encodes the appropriate amino acid sequence. The design and production of nucleic acids encoding a desired amino acid sequence is well known to those of skill in the art based on standardized codons. In preferred embodiments, the codons selected for encoding each amino acid may be modified to optimize expression of the nucleic acid in the host cell of interest. Codon preferences for various species of host cell are well known in the art.

The present invention further provides a therapeutic composition, or a method of regulating osteoclastogenesis thereof, comprising a pharmaceutically or therapeutically acceptable excipients, and a modulator, small molecule, peptide, protein, drug, known or later discovered, that is capable of modulating an interaction of RYBP, or a fragment thereof, with the IVVY (SEQ ID NO:4) motif of RANK, or modulating any downstream effectors in the RANK signaling pathway through the interaction of RYBP, or a fragment thereof, with the IVVY (SEQ ID NO:4) motif of RANK. As used herein, the term "modulator" refers to any naturally-occurred or chemically synthesized, known or later discovered, compounds, small molecules, peptides, proteins, enzymes, and drugs.

In certain embodiments, the pharmaceutically or therapeutically acceptable excipients, carriers or vehicles in the composition of the present invention comprise any acceptable materials, and/or any one or more additives known in the art. Furthermore, the composition of the present invention can also be made in any suitable solutions and/or formulations for oral, parenteral, transdermal or transmucosal administrations.

The present invention may be understood more readily by reference to the following detailed description of the preferred embodiments of the invention and the Examples included herein. However, before the present peptides, compounds, compositions, and methods are disclosed and described, it is to be understood that this invention is not limited to specific nucleic acids, specific peptides or proteins, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

It is also to be understood that as used in the specification and in the claims, "a" or "an" can mean one or more, depending upon the context in which it is used. Thus, for example, reference to "a cell" can mean that at least one cell can be utilized.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Cell lines, Mice and Preparation of Primary BMMs 293T and RAW264.7 cells were obtained from The American Type Culture Collection (ATCC). 293GPG and Plat-E retroviral packaging cells were kindly provided by Dr Daniel Ory (Washington University) and Dr Toshio Kitamura (University of Tokyo), respectively. C57BL/6 and TNFR1−/−R2−/− double KO mice were purchased from Harlan Industries (Indianapolis, Ind.) and The Jackson Laboratory (Bar Harbor, Me.), respectively. Animals were bred and maintained in accordance with the regulations of the UAB institutional animal care and use committee. BMMs were isolated from long bones of 4-8 week old C57BL/6 or TNFR1−/−R2−/− mice as previously described (Feng et al., 2001).

Construction of an Osteoclast Precursor cDNA Library

An osteoclast precursor cDNA library was constructed using CloneMiner™ cDNA Library Construction System from Invitrogen (Carlsbad, Calif.). Briefly, mRNA was isolated from mouse primary BMMs and used as template for cDNA synthesis. Synthesized cDNA was size fractionated by column chromatography and the desired size of cDNA (>500 bp) was pooled and cloned into pDONOR™222 vector with BP Clonase™ to make Osteoclast Precursor cDNA Entry Library. pGBKT7 AD Vector of MATCHMAKER Two-Hybrid System 3 (Invitrogen) was converted to a Gateway® destination vector using Gateway® Vector Conversion System (Invitrogen). The whole set of cDNA clones was then transferred from the Osteoclast Precursor cDNA Entry Library into the modified pGBKT7 AD Vector to prepare an Osteoclast Precursor Two-Hybrid cDNA Library.

Two-Hybrid Screen

A 49-aa RANK segment (residues 498-546) containing the IVVY (SEQ ID NO: 4) motif (residues 535-538) was used as bait in the two-hybrid screening. A mouse cDNA region encoding this 49-aa RANK fragment was cloned in frame into pGBKT7 DNA-BD Vector of the MATCHMAKER Two-Hybrid System 3 (Invitrogen). The resulting plasmid was named as pGBKT7 DNA-BD-RANK. 8 ml of competent yeast cells (strain AH109), freshly prepared according to the protocol in the instruction manual, was combined with a freshly prepared DNA mixture containing 500 µg of pGBKT7 DNA-BD-RANK, 250 µg of the Osteoclast Precursor Two- Hybrid cDNA Library and 20 mg of herring testes carrier DNA. The yeast-DNA complex was thoroughly mixed by vortexing and subsequent transformation steps were performed following the instructions in the manual. AH109 transformants were selected under medium stringency condition by plating the transformation mixtures on the medium-stringency medium (SD/-His/-Leu/-Trp medium) in 150-mm plates. The plates were incubated upside down at 30° C. until blue colonies appeared and/or grown big enough for further analysis. DNA was isolated from blue yeast colonies for transformation into E. Coli. DNA was then isolated from a large number of bacterial colonies derived from each blue yeast colony and sequenced to reveal the identity of the gene(s) encoding the potential RANK interacting partners.

Construction of Deletion Mutants and Site-directed Mutagenesis

Construction of internal deletion and site-directed mutagenesis were performed using the QuickChange™ Site-directed Mutagenesis Kit (Stratagene). The deleted regions and point mutations were confirmed by sequencing and other regions in the cDNA were sequenced to confirm that no mutations were introduced by PCR amplification during the experimental manipulation.

Co-Immunoprecipitation Assays 293T cells were cultured in DMEM containing 10% heat-inactivated fetal bovine serum (HI-FBS) and penicillin/streptomycin (culturing medium). Cells grown near confluence were lifted and replated at density of $5\times10^6$ cells/dish in 100-mm tissue culture dishes the day before transfection. Total 8 µg plasmid was transfected into 293T cells using Lipofectamine™ in combination of Plus® Reagent (Invitrogen). Briefly, 8 µg plasmid was mixed with 20 µl Plus®Reagent before addition of 350 µl DMEM. The mixture was incubated at RT for 15 min and then added with 380 µl freshly prepared Lipofectamine™ Reagent (Lipofectamine™ Reagent+350 µl DMEM). The complete transfection solution was further incubated at RT for 15 min before being added to one dish of 293T cells which was washed with DMEM twice immediately before the addition of the solution. The cells were incubated at 37° C. for 3 hrs before addition of 6.5 ml culturing medium and the incubation continued overnight. Next day, the medium containing the DNA/transfection reagents was replaced with fresh culturing medium. The transfected cells were cultured for one more day before lysis with IP Lysis Buffer (0.5M EDTA, 1M Tris-HCl pH8.0, 5M NaCl, 10% NP-40 and 10% Glycerol) for Co-IP assays. 30 µg protein from each lysate was mixed and then incubated with 3 µg anti-HA antibody or anti-Myc antibody from Clontech Laboratories, Inc (Mountain View, Calif.) at 4° C. on a rotating apparatus overnight. Next day, 50 µl of Protein-G beads, which was freshly washed with IP Buffer and then resuspended with IP Buffer (1:1 ratio), was added to the mixture and the incubation continued at 4° C. on a rotating apparatus for 2 hrs. Then, the beads were spun down and washed with IP buffer 5 times. Every time, the beads resuspended in IP buffer were incubated at 4° C. on a rotating apparatus for 15 min before being spun down again. After the final washing, supernatant was removed and the beads were resuspended with 35 ul of SDS Sample Buffer from Cell Signaling Technology (Danvers, Mass.). The samples were boiled for 5 min for Western blot analysis as described below.

Western Blot Analysis

Western blot analysis was performed as previously described (Xu et al., 2006; Liu et al., 2004). RAW264.7 cells cultured in DMEM containing 10% HI-FBS and penicillin/streptomycin were treated with RANKL (100 ng/ml) for various times before being lysed for Western blot analysis with anti-RYBP antibody from Abcam Inc (Cambridge, Mass.). Primary BMMs were normally cultured in α-MEM containing 10% HI-FBS and penicillin/streptomycin in the presence of M-CSF (44 ng/ml). Uninfected BMMs or BMMs infected with retrovirus encoding siRNA and/or tagged-RYBP were cultured in the presence of M-CSF (44 ng/ml) with or without RANKL (100 ng/ml) for various times and then lysed for Western blot analysis. For Western blot analysis of IP complex, all 35 µl of the eluted proteins from each IP assay was loaded for Western blot analysis with anti-HA antibody (Clontech Laboratories, Inc), anti-Myc antibody (Clontech Laboratories, Inc), anti-RYBP (Abcam Inc) antibody and anti-β-actin antibody (Santa Cruz Biotechnology).

In vitro Osteoclastogenesis Assays

Primary BMMs were cultured in 24-well tissue culture plates ($5\times10^4$ cells/well) with a-MEM containing 10% heat-inactivated FBS in the presence of 0.02 volume of culture supernatant of M-CSF-producing cells (final M-CSF concentration 44 ng/ml) (Takeshita et al., 2000) and 100 ng of GST-RANKL (Lam et al., 2000). Osteoclasts began to form on day 3 and cultures were stained for TRAP activity on day 5 using a commercial kit (Sigma, 387-A).

Retroviral Infection of Primary BMMs

293GPG cells were cultured in DMEM with 10% HI-FBS supplemented with tetracycline, puromycin, G418 and penicillin/streptomycin as previously described {2222}. Plat-E cells were cultured in DMEM with 10% HI-FBS supplemented with puromycin, blasticidin and penicillin/streptomycin as previously described {Morita, 2000 3155/id}. The retroviral vectors were transiently transfected into 293GPG cells or Plat-E cells using Lipofectamine Plus Reagent (Invitrogen). Virus supernatant was collected at 48, 72 and 96 h after transfection. Cells were then infected with virus for 24 hours in the presence of M-CSF (220 ng/ml) and 8 µg/ml polybrene. Cells were further cultured in the presence of M-CSF (220 ng/ml) and 2 µg/ml puromycin for selection and expansion of transduced cells. Selected cells were subsequently used for various studies.

Immunofluorescence Assays $1\times10^5$ BMMs were plated on polylysine coated coverslips in 6-well plates and the cultures were treated with M-CSF (44 ng/ml) alone or M-CSF (44 ng/ml) plus RANKL (100 ng/ml) for various times. TNFR1-/-R2-/- BMMs infected with virus encoding chimeric receptors were treated with MCSF (44 ng/ml) alone or M-CSF (44 ng/ml) plus TNF-α(10 ng/ml) for various times. Cells were fixed with 3% formaldehyde solution in PBS for 45 min at RT, and treated with 0.5% Triton X-100 in PBS for 2 min, and blocked with 1% BSA for 30 min at RT. Cells were then incubated with a Rabbit anti-RYBP polyclonal antibody from Abcam Inc (Cat# ab5976, 1:250 dilution in Blocking Buffer) for 1 hrs at RT, washed with PBS for 5 min (3 times) and blocked again with 1% BSA for 30 min at RT. Cells were further incubated with the Goat polyclonal to Rabbit IgG-H&L (FITC) second antibody from Abcam Inc (Cat# ab6717, 1:500 dilution in Blocking Buffer). Coverslips were washed with PBS for 5 min (3 times) and mounted with VECTASHIELD Mounting Medium with DAPI with DAPI (Ca# H-1200) from Vector Laboratories (Burlingame, Calif.). Coverslips were then subjected to confocal imaging using Leica DMIRBE Inverted UV SP1 Confocal Microscope System with Leica Confocal Software at UAB Imaging facility. Recombinant mouse TNFα (410-TRNC-050) was from R&D Systems (Minneapolis, Minn.).

Microarray Analysis

BMMs expressing Ch-WT or Ch-IVVY (SEQ ID NO: 4) were plated in six 60-mm tissue culture dishes and treated with M-CSF (44 ng/ml) and TNFα (10 ng/ml) for 24 hours. Total RNA was isolated from the six dishes and pooled. The RNA sample preparation was repeated independently two more times. Three sets of total RNA samples prepared from three independent assays were subject to microarray analysis using Mouse Genome 430 2.0 Array at the UAB Microarray Shared Facility. The raw data sets were obtained through GeneChip Operating Software (GCOS, Affymetrix, CA, USA) and loaded into the ArrayAssist and GeneSpring WG software (Agilent Technologies, CA, USA) for background subtraction and normalization by GC-robust multichip analysis (RMA) (Wu et al., 2004). The p-values were obtained by an unpaired t-test assuming unequal variance. Various gene lists with different fold changes or functions criteria were further filtered by minimum intensity and by presence/absence (P/A) calls. The resulting lists were used to generate heatmap and clusters through hierarchical clustering methods.

Semi-quantitative RT-PCR

Primary BMMs were treated with M-CSF (44 ng/ml) and RANKL (100 ng/ml) for 24 hours. Cells were either lysed for total RNA isolation immediately after the 24-hrs treatment or were further cultured with lysed M-CSF (44 ng/ml) for 2 or 4 more days before lysis. Primary BMMs expressing Ch-WT or Ch-Mu were treated with M-CSF (44 ng/ml) and TNF (10 ng/ml) for 24 hours. Similarly, cells were either lysed for total RNA isolation immediately after the 24-hrs treatment or were further cultured with lysed M-CSF (44 ng/ml) for 2 or 4 more days before lysis. Reverse transcription was performed with reserve transcriptase from Invitrogen using 1 µg total RNA. 1/30 of the reverse transcription reaction mixture was used to perform PCR to assess the levels of mRNA for Mmp9, Ctsk, TRAP and Car2 genes.

Identification and Characterization of RYBP as a Protein Interacting with the RANK IVVY (SEQ ID NO: 4) Motif The RANK IVVY (SEQ ID NO:4) motif plays a pivotal role in mediating the osteoclast lineage commitment by activating an essential downstream signaling pathway(s) through recruiting a signaling molecule (Xu et al., 2006). To identify the signaling protein, the two-hybrid screen was performed. In order to ensure success in obtaining the novel protein, it is critical to use an osteoclast precursor cDNA library for two-hybrid screening. Given that no such library was commercially available, an osteoclast precursor cDNA library was constructed using CloneMiner™ cDNA Library Construction System from Invitrogen (Carlsbad, Calif.). A mouse cDNA region encoding a 49-aa RANK fragment (residues 498-546), which contains the RANK motif (IVVY, SEQ ID NO:4, 535-538), was cloned into pGBKT7 DNA-BD Vector of MATCHMAKER Two-Hybrid System 3 as bait for two-hybrid screening (FIG. 1A) (FIG. 6). Three rounds of screening (a total of 3.6×106 independent clones) of the osteoclast precursor cDNA library yielded 14 positive clones encoding proteins capable of interacting with the RANK motif in yeast. Additional assays involving transformation of the bait construct and each of the isolated clones back into yeast revealed that 3 out of the 14 clones were false positives. The remaining 11 clones were also sequenced, revealing that several clones encode the same proteins (Table 1).

TABLE 1

Prioritization of Candidate Proteins Encoded by Clones from Two-Hybrid Screening

| Clone Name | Clones became blue on the same day colony formation | | | | | | | | Clones became blue one day after colony formation | | |
|---|---|---|---|---|---|---|---|---|---|---|---|
| | S1-1 | S1-2 | S1-3 | S2-1 | S3-1 | S3-2 | S1-4 | S3-3 | S1-5 | S1-6 | S3-4 |
| Candidate Proteins | GB: BC080287 Ring1 and YY1 bind Protein (RYBP) | | | | | | GB: BC050102 ATP-binding Cassette | | GB: AC120837 A novel gene in Chromosome 11 | GB: BC003220 E2F Transcription Factor | GB: BC006722 Heat Shock Protein 8 |
| Prioritized Order | #1 | | | | | | #2 | | #3 | #4 | #5 |

Moreover, some clones became blue on the same day when they formed on the plates while others became blue one day after colony formation. This indicates that proteins encoded by these clones exhibit different affinities for the bait (the novel RANK motif) since the time a clone takes to become blue should be proportional to its affinity for the bait. Based on the affinity of these proteins for the bait and the number of clones encoding them, these proteins were prioritized in numerical order with #1 as the protein which is most likely to be the functional one involved in the RANK motif-mediated signaling (Table 1).

RYBP was assigned #1 since it has the highest affinity for the bait and was represented in 6 independently isolated clones (Table 1). As such, the potential of RYBP as a signaling molecule interacting with the IVVY (SEQ ID NO:4) motif was examined to regulate osteoclastogenesis. Western blots showed that RYBP is highly expressed in osteoclast precursors and during osteoclast differentiation (FIG. 1B). It was then determined whether the interaction between the RANK fragment and RYBP seen in yeast also occurs in mammalian cells. the cDNA region encoding the bait was cloned into pCMV-Myc vector (BD Biosciences Clontech) to generate Myc-RANK (FIG. 1C). The full-length RYBP cDNA was subcloned into pCMV-HA (BD Biosciences Clontech) vector to prepare HA-RYBP (FIG. 1C). Myc-RANK, HA-RYBP and two empty control vectors (HA-Vector and Myc-Vector) were cotransfected into 293 cells in different combinations (FIG. 1D). Transfected cells were lysed for coimmunoprecipitation with anti-HA antibody. The precipitates were then subject to Western analysis with anti-Myc antibody. While the assays cotransfected with HA-Vector plus Myc-Vector, HA-Vector plus Myc-RANK, or HA-RYBP plus Myc-Vector failed to coimmunoprecipitate HA-RYBP (lanes 1, 2 and 3 in FIG. 1D), the assay with both HA-RYBP and Myc-RANK gave rise to a positive band for HA-RYBP (lane 4 in FIG. 1D), indicating that RANK interacts with RYBP in mammalian cells. To further verify the interaction between RANK and RYBP, the same cell lysates were coimmunoprecipitated with anti-Myc antibody and then the precipitates were analyzed by Western analysis with anti-HA antibody (FIG. 1E). In this assay, a band was also recognized by anti-HA antibody in the precipitate from cells cotransfected with HA-RYBP and Myc-RANK (lane 4 in FIG. 1E), but not in those from the control cells (lanes 1, 2 and 3 in FIG. 1E), providing additional evidence that RANK interacts with RYBP.

Next, it was determined whether the IVVY (SEQ ID NO:4) motif in the RANK region is specifically responsible for interaction with RYBP. Myc-mRANK was constructed in which the same RANK cDNA region bearing the inactivating mutation in the novel motif (IVAF, SEQ ID NO:7, L535-538) was subcloned into pCMV-Myc vector (FIG. 1F). HA-RYBP was cotransfected with either Myc-RANK or Myc-mRANK into 293 cells. Cell lysates were coimmunoprecipitated with anti-Myc antibody and then the precipitates were analyzed by Western analysis with anti-HA antibody. While cotransfection of HA-RYBP with Myc-RANK yielded a positive band (lane 1, FIG. 1G), the assay with HA-RYBP and MycmRANK failed to do so (lane 2, FIG. 1G), indicating that the interaction between RANK region and RYBP is specifically mediated by the IVVY (SEQ ID NO: 4) motif.

Figure 2B:
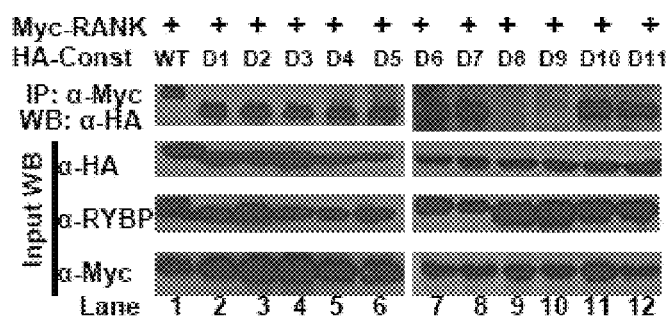

Identification of Specific RYBP Domains Responsible for Interaction with the RANK IVVY (SEQ ID NO:4) Motif To identify specific RYBP domains mediating the interaction with the RANK IVVY (SEQ ID NO:4) motif, 11 deletion mutants of RYBP (D1-D11) were generated and around 20-aa region was deleted in each mutant (FIG. 2A)(Figure S2). Deletion of a small region was intended to minimize the effect of the deletion on the structural integrity of RYBP since the 3-dimensional structure may be important for the interaction. In addition, a systematic generation of the 11 deletion mutants would enable us to identify the region mediating the interaction in an unbiased fashion. These deletion mutants were subcloned into pCMV-HA vector. These constructs were cotransfected with Myc-RANK into 293T cells to perform coimmunoprecipitation assays as described above in FIG. 1. The data show that D8 and D9 were unable to interact with RANK (lanes 9 and 10, FIG. 2B), indicating that the segments deleted in these two constructs are important for the interaction.

Figure 2C:
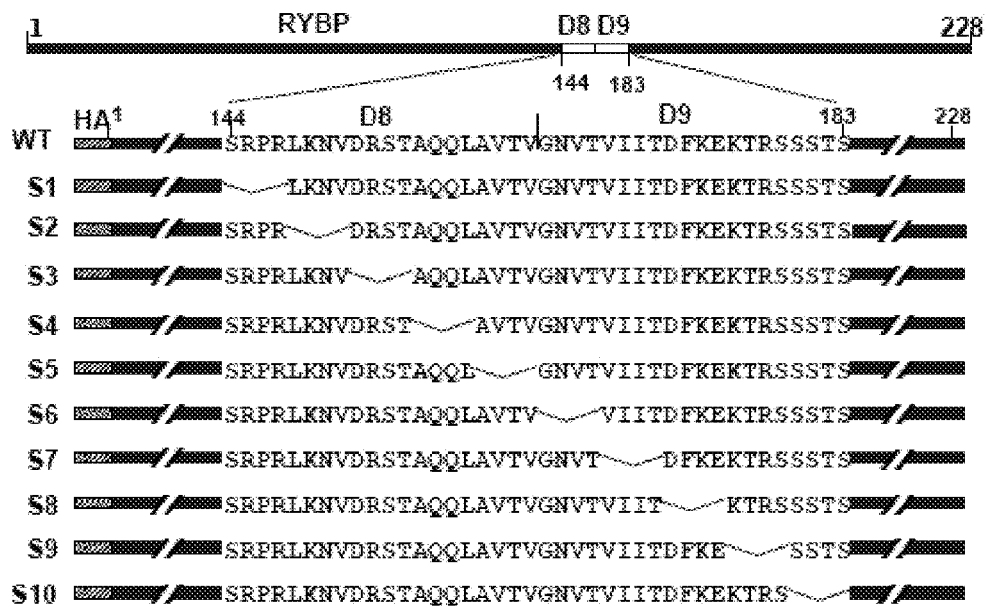
Figure 2D:
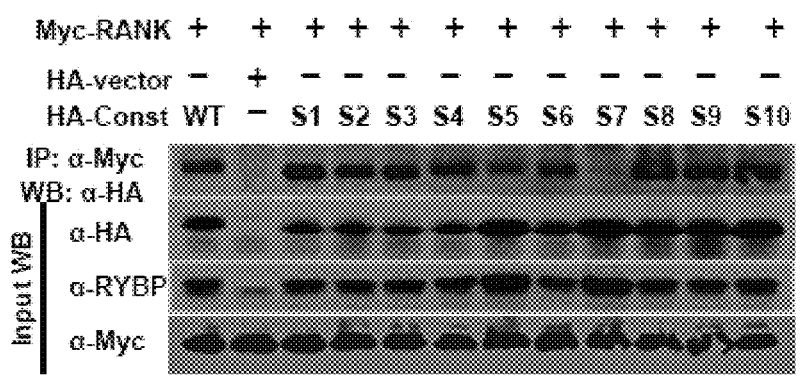
Figure 2E:
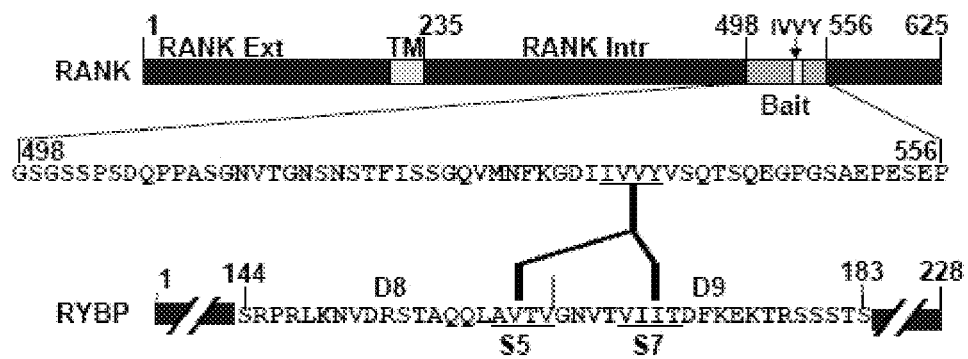

The sequence of the 40-aa region deleted in D8 and D9 is shown in FIG. 2C. To further locate the specific domain(s) responsible for the interaction, 10 more deletion mutants were prepared in each of which a 4-aa segment is deleted (S1-S10) (FIG. 2C). Coimmunoprecipitation assays were performed with the small deletion mutants and Myc-RANK. The assays involving immunoprecipitation with anti-Myc antibody followed by Western analysis with anti-HA antibody demonstrated that while S5 and S7 exhibited reduced capacity to interact with RANK, the amino acid residues deleted in S7 are more critical than those deleted in S5 in mediating the interaction with RANK (FIG. 2D). The location and sequence of the two functional domains are depicted in FIG. 2E.

RYBP is Functionally Involved in RANKL-induced Osteoclastogenesis

Figure 8:
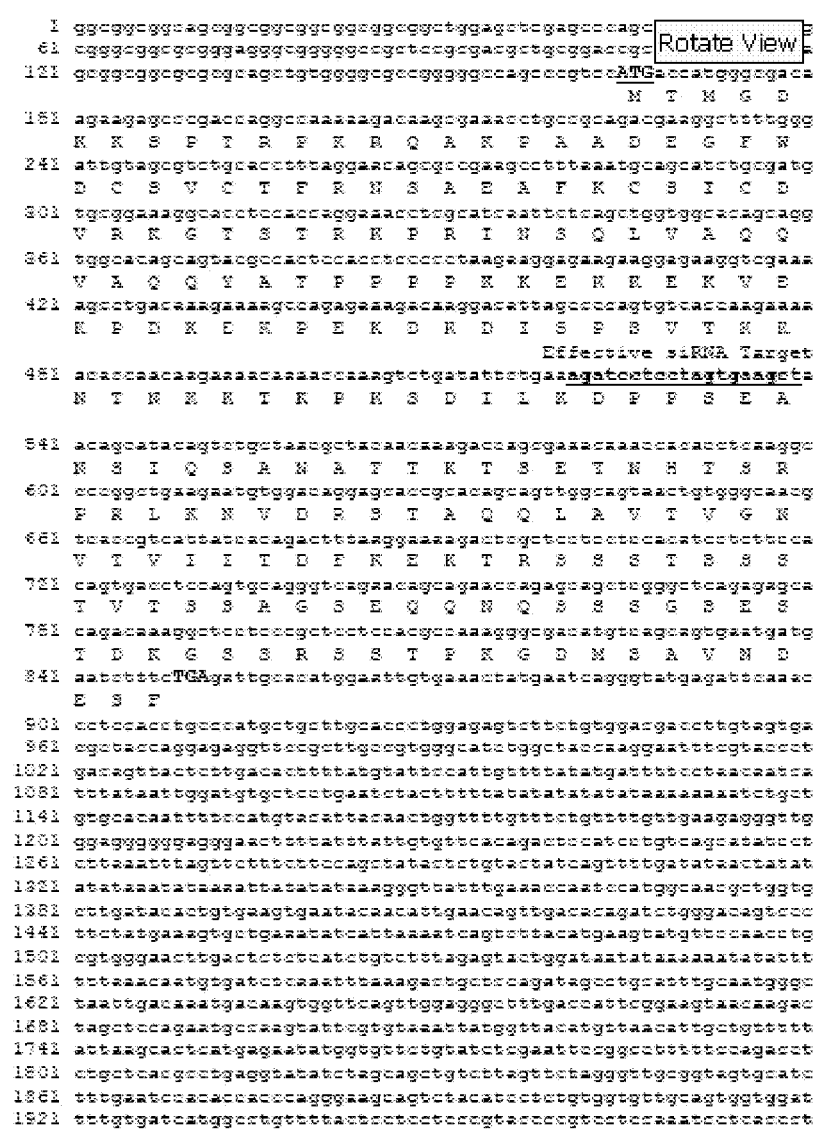

To functionally determine RYBP is involved in the IVVY (SEQ ID NO:4) motif-mediated osteoclastogenesis, RYBP expression in primary BMMs was knocked down using the RNAi technology. While primary BMMs are extremely difficult to transfect, they can be efficiently infected by retrovirus. Several retrovirus-based expression systems including the ΔU3nlsLacZ-293GPG system were used to express exogenous genes in primary BMMs (Ory et al., 1996; Feng et al., 2001; Xu et al., 2006). To achieve a high level expression of siRNA to efficiently down-regulate RYBP expression, a retroviral siRNA expression vector named pPower-siRNA based on ΔU3nlsLacZ (Ory et al., 1996)(FIG. 3A) was developed. ΔU3nlsLacZ contains a strong CMV promoter in place of U3 of 5' LTR to attain higher levels of transcripts than most natural 5' LTR when transfected into 293 cells-based packaging cells (Ory et al., 1996). More than 20 sequences in the gene encoding RYBP were selected for potential siRNA target sequences by the siRNA target finder provided by Ambio, Inc (Austin, Tex.) and subcloned them into pPower-siRNA between Xho and Bam HI. Retrovirus encoding these siRNAs were prepared by transfecting these as described in (Ory et al., 1996; Feng et al., 2001) and used to infect primary BMMs. The infected cells were lysed for Western analysis to examine the downregulation of RYBP expression. Several functional siRNA sequences were obtained and the one with the highest efficiency in suppression of RYBP gene expression was chosen for the subsequent assays (FIG. 3A) (FIG. 8).

Figure 3A:
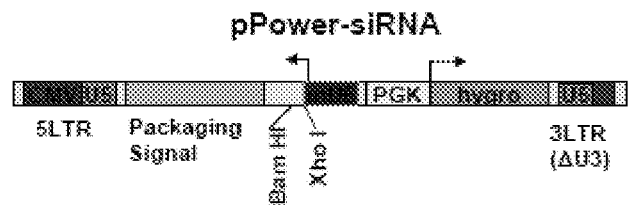
FIG. 3 illustrates functional involvement of RYBP in osteoclast differentiation. (A) Schematic illustration of pPower-siRNA retroviral vector. LTR: long terminal repeat; CMV: the cytomegalovirus promoter; mU6: the murine U6 promoter; PGK: the phosphoglycerate kinase promoter; Hygro: hygromycin. (B) BMMs were uninfected (UN) or infected with retrovirus expressing scramble control siRNA (Control: 3'-UCUAGGAGGAUCACUUCGA-5' (SEQ ID NO:8)) or siRNA (3'-UCUAGGAGGAUCACUUCGA-5' (SEQ ID NO:9)) targeting RYBP for 24 hrs. 2 days after infection, cells were lysed for Western blot analysis with anti-RYBP antibody. Loading control was performed with anti-β-actin antibody (β-actin). (C) Uninfected BMMs (UN) and BMMs infected with retrovirus expressing scramble control siRNA (Control) or siRNA targeting RYBP (siRNA) described in (B) were treated with M-CSF (44 ng/ml) and RANKL (100 ng/ml) for 4 days. The culture was stained for TRAP. Top row is the image of the TRAP-stained culture plate. Bottom row shows the high power view of a representative area from each treatment of the TRAP-stained culture. (D) Strategy for knocking down the endogenous RYBP (SEQ ID NO: 25) by siRNA (SEQ ID NO: 8) without affecting the expression of exogenous HA-tagged WT RYBP (RYBP-HA (SEQ ID NO: 26)) or mutant RYBP (dRYBP-HA (SEQ ID NO: 26)). The selected siRNA targets the RYBP mRNA region which encodes DPPSEA (SEQ ID NO:10). The same region of RYBP-HA and dRYBP-HA constructs were altered so that they produce mRNA which are significantly different from siRNA but encode the same amino acid sequence.
FIG. 3D discloses 'VIIT' as SEQ ID NO: 5. (E) BMMs were uninfected (Uninfected) or infected with retrovirus expressing siRNA (siRNA) targeting RYBP for 24 hrs. In addition, BMMs infected with retrovirus expressing siRNA were co-infected with virus expressing RYBP-HA (siRNA/RYBP-HA) or dRYBP-HA (siRNA/dRYBPHA) for 24 hrs. 2 days after infection, cells were lysed for Western blot analysis with anti-RYBP antibody or anti-HA antibody. Loading control was performed with anti-β-actin antibody (β-actin). (F) Uninfected BMMs (UN) and BMMs infected with various viruses (siRNA, siRNA/RYBP-HA or siRNA/dRYBP-HA) as described in (E) were treated with M-CSF (44 ng/ml) and RANKL (100 ng/ml) for 4 days. The culture was stained for TRAP. Top row is the image of the TRAPstained culture plate. Bottom row shows the high power view of a representative area from each treatment of the TRAP-stained culture.
Figure 3B:
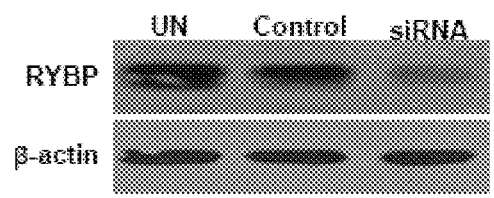
Figure 3C:
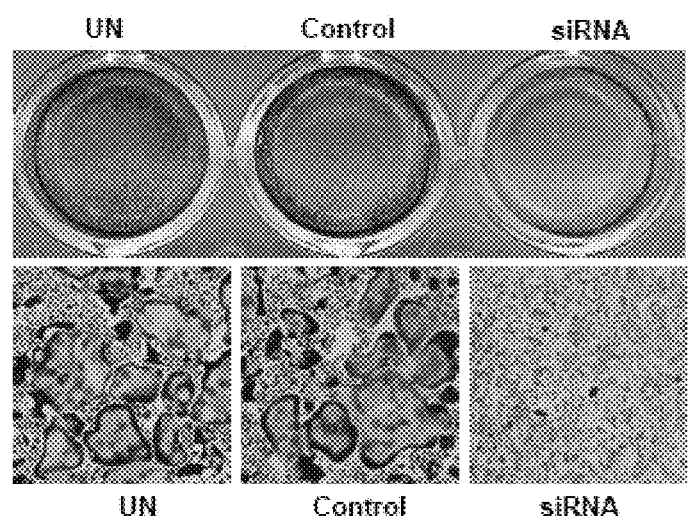

A scrambled siRNA sequence was designed to use as control (FIG. 3A). BMMs were uninfected or infected with retrovirus expressing scrambled RNA or RYBP siRNA. An aliquot of infected cells were lysed for assessment of levels of RYBP expression, whereas the remaining cells were plated and treated with M-CSF and RANKL to stimulate osteoclastogenesis. As shown in FIGS. 3B and 3C, the selected siRNA significantly suppressed RYBP expression in osteoclast precursors and the siRNA-mediated downregulation of RYBP expression inhibited osteoclastogenesis. In contrast, neither reduction of RYBP expression nor failure in osteoclastogenesis was seen in uninfected cells or those infected with retrovirus encoding the scrambled control sequence. These data indicate that RYBP is functionally involved in the RANK motif-mediated osteoclastogenesis.

Figure 3D:
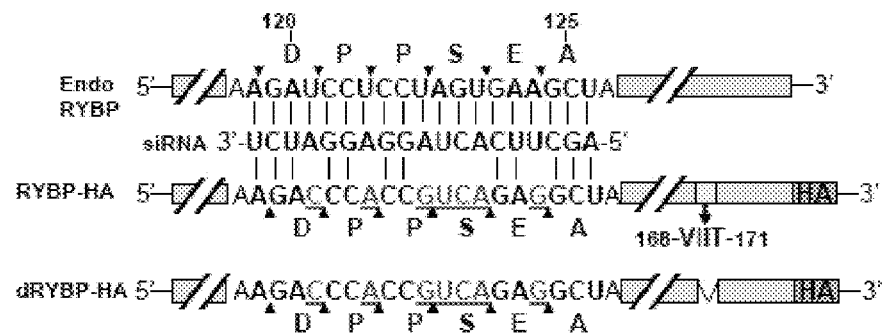
Figure 3E:
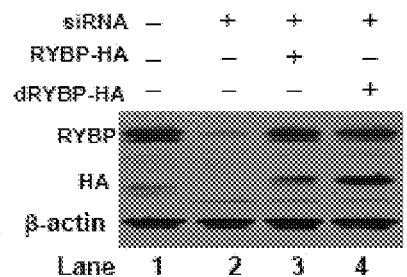
Figure 3F:
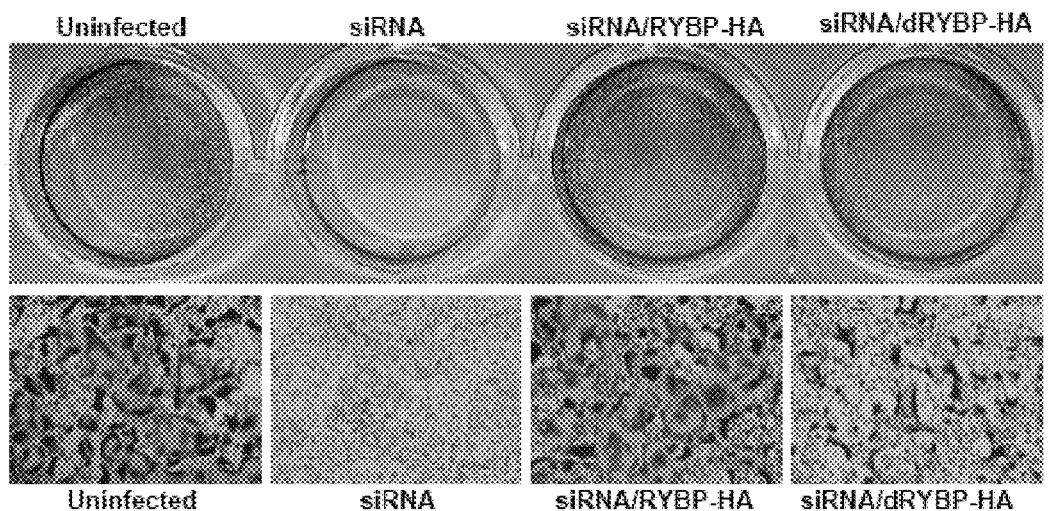

To further investigate the functional role of RYBP in osteoclastogenesis, rescue experiments were carried out, which aimed to address two important issues: 1) off-target effect of siRNA and 2) the functional significance of the RYBP domain shown to mediate its interaction with the RANK IVVY (SEQ ID NO:4) domain. This rescue study requires an effective strategy to reduce the endogenous RYBP in BMMs and simultaneously express an exogenous WT or mutant RYBP. RNAi is a highly sequence-specific process. It has been established that a single-nucleotide mismatch can significantly render a siRNA inactive in mammalian cells (Hall, 2004; Amarzguioui et al., 2003; Pusch et al., 2003). Thus, this can be achieved by introducing multiple mutations within the targeting sequence in the constructs encoding exogenous WT or mutant RYBP and these mutations are selected so that the resulting sequence encode the same amino acids. Based on these principles, we prepared two constructs: RYBP-HA and dRYBP-HA (FIG. 3D). RYBP-HA encodes WT RYBP linked containing a HA tag at its C-terminus whereas dRYBP-HA expresses a HA-tagged mutant RYBP in which the domain (VIIT168-171) responsible for interacting with RANK was deleted (FIG. 3D). Moreover, in both constructs, the coding region targeted by the siRNA was considerably mutated (7 out of 19 nt) in a manner that the introduced mutation do not alter the amino acid sequence (FIG. 3D).

These constructs were cloned into retroviral expression vectors for expression in BMMs. As shown in FIG. 1E, while retrovirally expressed RYBP siRNA dramatically knocked down endogenous RYBP expression, addition of the retrovirus encoding HA-tagged WT RYBP or mutant RYBP efficiently increased RYBP levels. The re-expressed RYBP are HA-tagged exogenous RYBP since HA antibody recognizes the protein (FIG. 1E). Importantly, the re-expression of WT RYBP-HA effectively rescued osteoclastogenesis while the dRYBP-HA exhibited impaired capacity to restore osteoclastogenesis (FIG. 1F), further demonstrating that RYBP plays a functional role in the RANK-mediated osteoclastogenesis. Specifically, these data indicate that the failed osteoclastogenesis from BMMs retrovirally transduced with RYBP siRNA directly result from the reduced levels of RYBP, not due to the off-target effects. Secondly, the data demonstrated that the RYBP domain identified by co-IP experiments in FIG. 2 is functionally involved in the RANK-mediated osteoclastogenesis.

IVVY (SEQ ID NO:4) Motif Regulates RYBP Intracellular Translocation during RANKL-mediated Osteoclastogenesis Having established that RYBP not only interacts with the IVVY (SEQ ID NO:4) motif but is also functionally involved in osteoclastogenesis, the molecular mechanism by which RYBP modulates RANKL-mediated osteoclastogenesis were not determined. RYBP has been shown to be a nuclear protein and regulate gene expression by acting as a protein interacting with members of the PcG and various transcription factors (Garcia et al., 1999; Trimarchi et al., 2001; Schlisio et al., 2002; Sawa et al., 2002). However, given that the current work has demonstrated that RYBP is capable of interacting with RANK, which is a well-documented transmembrane protein, suggesting that RYBP may also be present in the cytoplasm and acts as a signaling molecule to transmit the membrane-proximal signal to regulate nuclear events. Immunofluroescence staining assays were performed to examine the subcellular location of RYBP during the 4-day in vitro osteoclastogenesis.

Figure 4A:
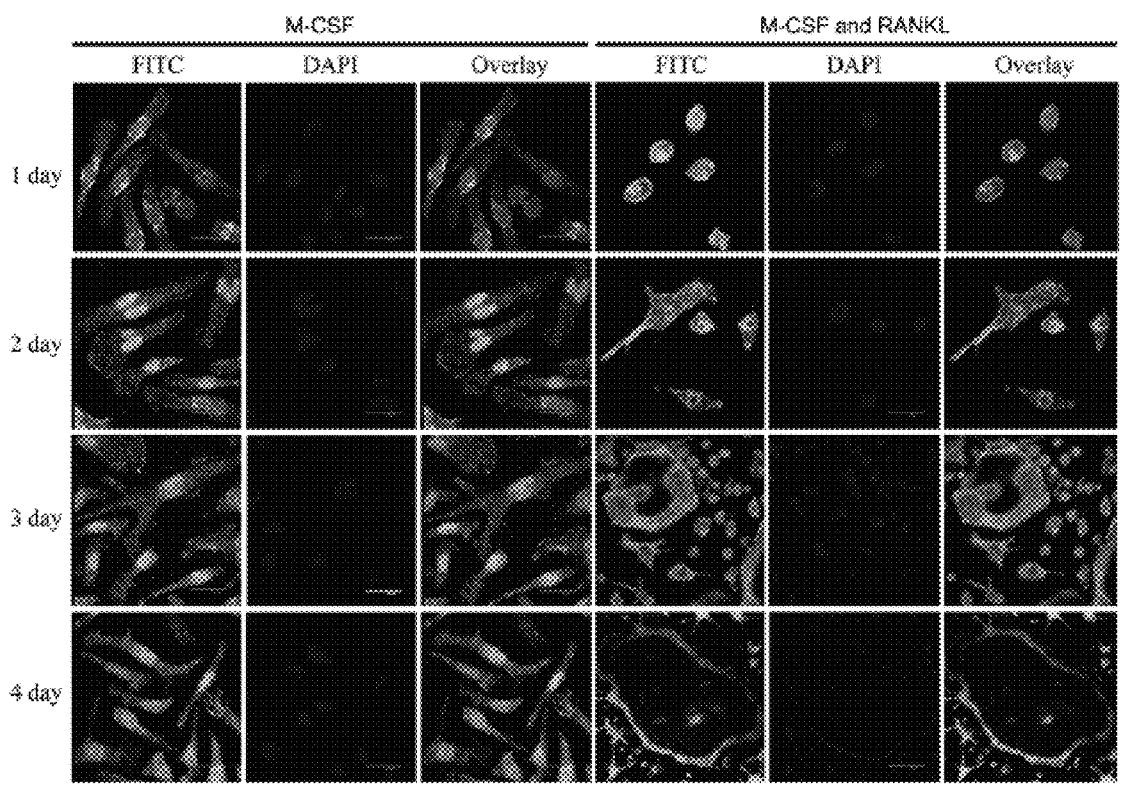
FIG. 4 illustrates that the IVVY (SEQ ID NO:4) motif mediates the RANKL-induced intracellular translocation of RYBP during osteoclastogenesis. (A) RANKL stimulates intracellular translocation of RYBP during osteoclastogenesis. BMMs were treated with M-CSF (44 ng/ml) alone (Control) or with M-CSF (44 ng/ml) and RANKL (100 ng/ml) (RANKL Treatment) for 1d, 2d, 3 day or 4 days. Cells were then fixed and stained with DAPI or immunostained with anti-RYBP antibody. (B) BMMs isolated from TNFR1−/− 2−/− mice were infected with virus encoding a chimeric receptor consisting of the TNFR external domain linked to the transmembrane and intracellular domains of mouse wild-type RANK (WT) or virus encoding a chimeric receptor consisting of the TNFR external domain linked to the transmembrane and intracellular domains of mouse RANK containing inactivating mutation in the IVVY (SEQ ID NO:4) motif (Mu). Infected cells were treated with M-CSF (44 ng/ml) and TNF (10 ng/ml) for 1 hrs, 2 hrs, 4 hrs, 8 hrs, 1d and 2d. Cells were then fixed and stained with DAPI staining or immunofluorescence staining with anti-RYBP antibody.

As shown in FIG. 4A, while RYBP is present both in the cytoplasm and in the nucleus of BMMs treated with M-CSF only, the nucleus has significantly more RYBP than the cytoplasm (left panel). Moreover, the spindle-like shape of the cells and the pattern of RYBP subcellular location remain unchanged during the 4-day M-CSF treatment. In contrast, one-day RANKL treatment induced the translocation of RYBP from the nucleus to the cytoplasm (right panel, FIG. 4A). In particular, a significant amount of RYBP moved to the plasma membrane, presumably resulting from the interaction with RANK. Interestingly, on day 2, a portion of RYBP moved back to the nucleus and they appear to be located primarily at the nuclear periphery (right panel, FIG. 4A). On day 3, cells had begun to fuse to form multinucleated osteoclasts in which RYBP was seen at the plasma membrane. In addition, nuclei also appeared to move to plasma membrane. On day 4, most nuclei had lined up together with the plasma membrane. On the last two days, RYBP was exclusively located at the plasma membrane and the nuclear membrane. It is also noted that RYBP was localized speckled nuclear bodies in cells treated with M-CSF for one day but RYBP was then distributed throughout the Nucleoplasm with longer M-CSF treatment (left panel, FIG. 4A).

Figure 9:
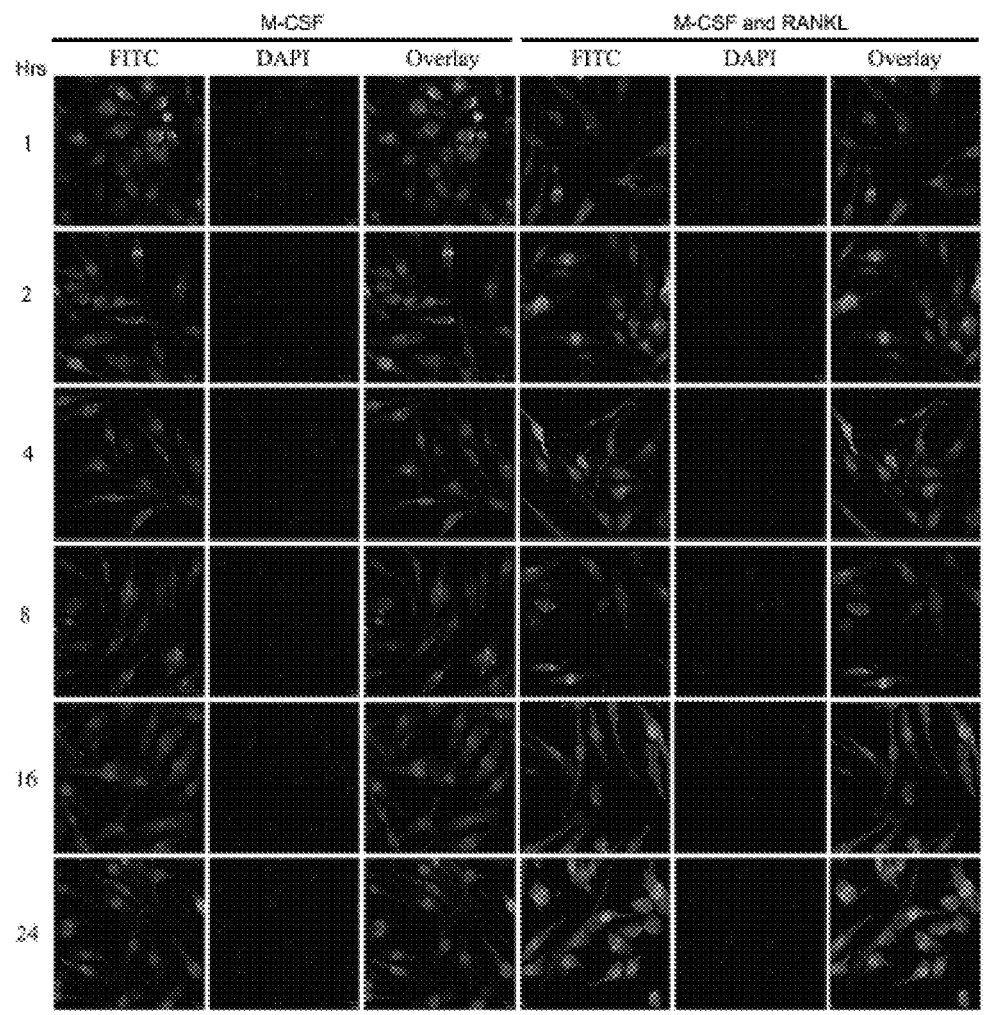
FIG. 9 illustrates that the IVVY (SEQ ID NO:4) motif mediates the RANKL-induced intracellular translocation of RYBP during osteoclastogenesis during the first 24 hours. BMMs were treated with M-CSF (44 ng/ml) alone (Control) or with M-CSF (44 ng/ml) and RANKL (100 ng/ml) (RANKL Treatment) for 1, 2, 4, 8, 16 or 24 hours. Cells were then fixed and stained with DAPI or immunostained with anti-RYBP antibody.

To further investigate RYBP intracellular translocation during the first 24 hours of the RANKL treatment, immunofluroescence staining assays were repeated with M-CSF (Control) or M-CSF plus RANKL for 1, 2, 4, 8, 16 and 24 hrs (FIG. 9). The assays indicated that a notable amount of RYBP proteins had moved out of the nucleus 8 hrs after RANKL treatment and a significant portion of RYBP proteins were located in the cytoplasm at the 16-hr RANKL treatment point. Similar to the previous assays in FIG. 4A, some of RYBP proteins had been localized at the plasma membrane 24 hrs after RANKL treatment (right panel, FIG. 9). In MCSF-treated control cells, RYBP was present in both the cytoplasm and the nucleus and there was no significant intracellular translocation of RYBP. However, cells were largely spherical at 1-hr M-CSF treatment but cells gradually become spindle-shaped with longer M-CSF treatment (Left panel, FIG. 9). In contrast, while cells treated with both M-CSF and RANKL during the first 16 hrs had a similar shape as those treated with M-CSF only, some of them become spherical again 24 hrs after RANKL treatment.

Figure 10A:
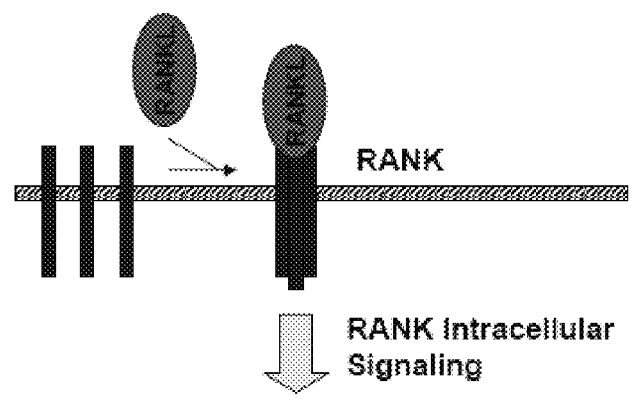
FIG. 10 illustrates how a chimeric receptor can be used to determine whether IVVY (SEQ ID NO: 4) mediates RYBP intracellular translocation in osteoclast precursors. (A) As a member of the TNFR family, RANK is activated by RANKL-induced trimerization. (B) As a surrogate, TNFα can induce the trimerization of the chimeric receptor to activate the RANK signaling required for osteoclast formation, function and/or survival. In addition, since TNFα can also regulate osteoclast formation and function, this approach requires the use of osteoclast precursors from TNFR1&R2 double knockout (TNFR1$^{-/-}$R2$^{-/-}$) mice to prevent potential signaling from TNFR. (C) Ch-WT is a chimeric receptor system consisting of the external domain of TNFR1 linked to the transmembrane and intracellular domains of wild-type RANK, while Ch-Mu is a mutant chimeric receptor system consisting of the external domain of TNFR1 linked to the transmembrane and intracellular domains of RANK containing inactivating mutations in the IVVY (SEQ ID NO: 4) motif. Thus, this chimeric receptor approach can be used as a tool to determine whether IVVY (SEQ ID NO: 4) mediates RYBP intracellular translocation in osteoclast precursors.
FIG. 10C discloses 'IVAF' as SEQ ID NO: 7.

Next, to investigate whether the IVVY (SEQ ID NO:4) motif specifically mediates the RYBP translocation was investigated, a chimeric receptor system consisting of the external domain of TNFR1 linked to the transmembrane and intracellular domains of RANK was used (Figure S5) (Liu et al., 2004; Xu et al., 2006). Briefly, as a member of the TNFR family, RANK is activated by RANKL-induced trimerization (FIG. 10A). As a surrogate, TNF can induce the trimerization of the chimeric receptor to activate the RANK signaling required for osteoclast formation, function and/or survival (FIG. 10B) (Liu et al., 2004; Xu et al., 2006). Since TNF can also regulate osteoclast formation and function, osteoclast precursors BMMs from TNFR 1 &R2 double knockout (TNFR1−/−R2−/−) mice were used to prevent potential signaling from TNFR.

Figure 4B:
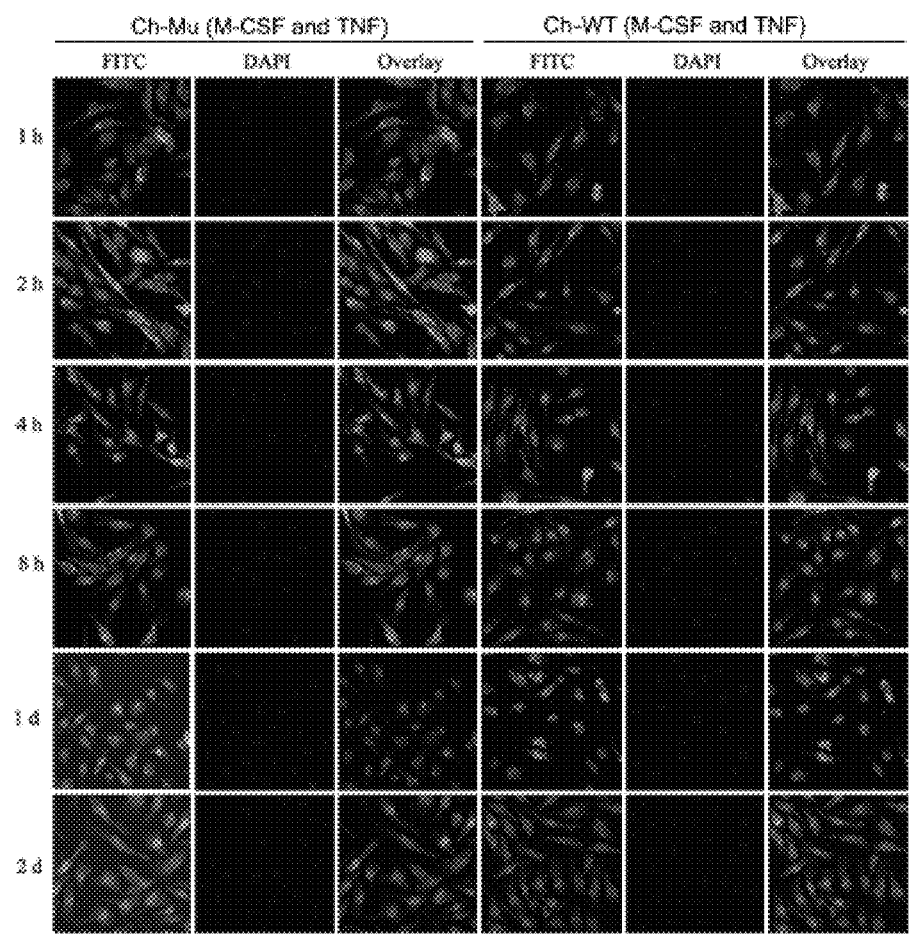
Figure 10B:
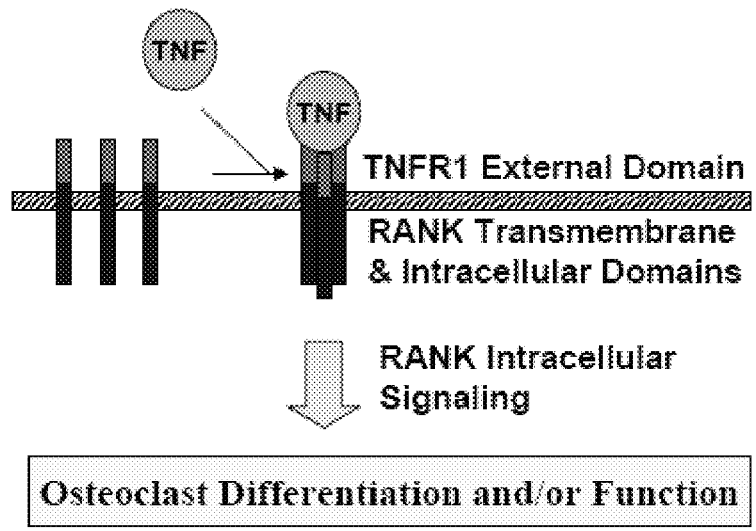
Figure 10C:
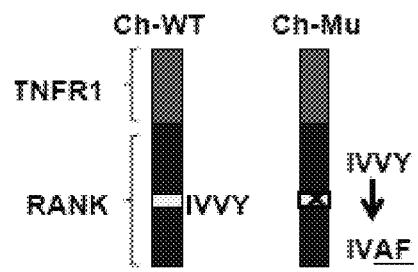

BMMs expressing Ch-WT or Ch-Mu were prepared using the retroviral approach as described previously (Liu et al., 2004; Xu et al., 2006) (FIG. 10B). The surface expression of the chimeric receptors was assessed by flow cytometric analysis (data not shown). Infected cells with similar levels of the chimeric receptor surface expression were treated with M-CSF (44 ng/ml) and TNF (10 ng/ml) for 1 hr, 2 hrs, 4 hrs, 8 hrs, 1 day or 2 days. The data demonstrated that Ch-WT gave rise to a similar pattern of RYBP intracellular translocation in response to TNF treatment (right panel, FIG. 4B) as endogenous RANK did in response to RANKL treatment (right panel, FIG. 4A and right panel, FIG. 4B). However, Ch-Mu, in which IVVY (SEQ ID NO:4) motif was inactivated, failed to induce RYBP intracellular translocation (left panel, FIG. 4B). These data indicate that the IVVY (SEQ ID NO:4) motif plays a critical role in mediating RYBP intracellular translocation, establishing the functional significance of the interaction between RYBP and the RANK IVVY (SEQ ID NO: 4) motif.

Identification of IVVY (SEQ ID NO:4)-regulated Genes by Microarray Analysis

As a protein interacting with members of the PcG family, RYBP has been shown to mediate transcriptional repression in reporter assays (Garcia et al., 1999). Moreover, RYBP also interacts with various transcription factors including YY1 (Garcia et al., 1999), members of the E2F family (Trimarchi et al., 2001; Schlisio et al., 2002), E4TF1/hGABP (Sawa et al., 2002) and ubiquitinated H2A (Arrigoni et al., 2006), which is associated with transcriptional repression (Li et al., 2007). These observations support that RYBP functions as a regulator of gene expression. Given that the data have established that the IVVY (SEQ ID NO:4) motif plays a critical role in osteoclastogenesis by interacting with RYBP, it is likely that RYBP may transmit the IVVY (SEQ ID NO:4) motif initiated signal to regulate gene expression required for osteoclastogenesis.

To determine whether the IVVY (SEQ ID NO:4) motif regulates gene expression in BMMs. BMMs expressing the chimeric receptor containing wild type RANK intracellular domain (Ch-WT) or mutant RANK bearing inactivating mutations in the IVVY (SEQ ID NO:4) motif (Ch-Mu) (FIG. 10B) were treated with M-CSF (44 ng/ml) and TNF (10 ng/ml) for 24 hrs. Total RNA was isolated for microarray analysis at the Microarray Shared Facility at the University of Alabama at Birmingham (UAB). The 3 chips in wild type groups and 3 in mutant group were clustered based on their expressions (FIG. 5A). The number of genes activated based different p values and fold changes were also listed (FIG. 5B). The microarray assays indicate that 203 genes that are significantly regulated by the IVVY (SEQ ID NO:4) motif (i.e. ≥1.1 fold change with p value <0.05) (FIG. 5B). The detailed information on these genes is provided in Table 2.

TABLE 2

List of genes regulated by the IVVY (SEQ ID NO: 4) motif

| Gene Title | Gene Symbol | Chromosome Number | Fold Change | Up or Down |
|---|---|---|---|---|
| matrix metallopeptidase 9 | Mmp9 | chr2 | 52.957066 | up |
| matrix metallopeptidase 9 | Mmp9 | chr2 | 35.26287 | up |
| carbonic anhydrase 2 | Car2 | chr3 | 15.665942 | up |
| cathepsin K | Ctsk | chr3 | 15.22314 | up |
| chemokine (C-X-C motif) ligand 3 | Cxcl3 | chr5 | 13.967028 | up |
| acid phosphatase 5, tartrate resistant | Acp5/TRAP | chr9 | 12.049807 | up |
| Cd200 antigen | Cd200 | chr16 | 9.085004 | up |
| G protein-coupled receptor 68 | Gpr68 | chr12 | 9.067647 | up |
| serine incorporator 2 /// hypothetical protein LOC100044221 | LOC100044221 /// Serinc2 | chr4 | 8.342579 | up |
| Tnf receptor-associated factor 1 | Traf1 | chr2 | 8.335335 | up |
| transmembrane 7 superfamily member 4 | Tm7sf4 | chr15 | 7.1823263 | up |
| vascular endothelial growth factor C | Vegfc | chr8 | 7.1291 | up |
| vascular endothelial growth factor C | Vegfc | chr8 | 6.6310782 | up |
| vascular endothelial growth factor C | Vegfc | chr8 | 5.5311403 | up |
| versican | Vcan | chr13 | 5.449619 | up |
| glypican 1 | Gpc1 | chr1 | 5.397397 | up |
| versican | Vcan | chr13 | 5.2082253 | up |
| myosin ID | Myo1d | chr11 | 5.0793095 | up |
| adrenergic receptor kinase, beta 2 | Adrbk2 | chr5 | 4.936684 | up |
| RIKEN cDNA 4833422F24 gene | 4833422F24Rik | chr2 | 4.8180194 | up |
| Rab38, member of RAS oncogene family | Rab38 | chr7 | 4.580771 | up |
| RIKEN cDNA 2610528A11 gene | 2610528A11Rik | chr14 | 4.5504866 | up |
| cyclin-dependent kinase inhibitor 2B (p15, inhibits CDK4) | Cdkn2b | chr4 | 4.53978 | up |
| Jun dimerization protein 2 | Jundm2 | chr12 | 4.353514 | up |
| Na+/H+ exchanger domain containing 2 | Nhedc2 | chr3 | 4.1892962 | up |
| myosin IB | Myo1b | chr1 | 4.1877007 | up |
| chaperone, ABC1 activity of bc1 complex like (S. pombe) | Cabc1 | chr1 | 4.010523 | up |
| met proto-oncogene | Met | chr6 | 3.9681833 | up |
| Rous sarcoma oncogene | Src | chr2 | 3.7441297 | up |
| adrenergic receptor kinase, beta 2 | Adrbk2 | chr5 | 3.7051468 | up |
| A kinase (PRKA) anchor protein 6 | Akap6 | chr12 | 3.6483796 | up |
| macrophage stimulating 1 receptor (c-met-related tyrosine kinase) | Mst1r | chr9 | 3.4987073 | up |
| purinergic receptor P2X, ligand-gated ion channel, 5 | P2rx5 | chr11 | 3.34429 | up |
| acid phosphatase, prostate | Acpp | chr9 | 3.1458142 | up |
| lymphocyte antigen 6 complex, locus I | Ly6i | chr15 | 3.1208453 | up |
| nuclear factor of activated T-cells, cytoplasmic, calcineurin-dependent 1 | Nfatc1 | chr18 | 3.054388 | up |
| G protein-coupled receptor 132 | Gpr132 | chr12 | 2.9648147 | up |
| metallothionein 2 | Mt2 | chr8 | 2.5575764 | up |
| orosomucoid 1 | Orm1 | chr4 | 2.438179 | up |
| SMAD specific E3 ubiquitin protein ligase 1 | Smurf1 | chr5 | 2.4253285 | up |
| N-myc downstream regulated gene 4 | Ndrg4 | chr8 | 2.3484612 | up |
| SLIT-ROBO Rho GTPase activating protein 3 | Srgap3 | chr6 | 2.2787986 | up |
| RIKEN cDNA 9030425E11 gene | 9030425E11Rik | chr9 | 2.2157958 | up |
| Gardner-Rasheed feline sarcoma viral (Fgr) oncogene homolog | Fgr | chr4 | 2.1882703 | up |
| calcitonin receptor | Calcr | chr6 | 2.1615038 | up |
| nuclear factor of activated T-cells, cytoplasmic, calcineurin-dependent 1 | Nfatc1 | chr18 | 2.1178071 | up |
| expressed sequence AW049765 | AW049765 | chr17 | 2.1107264 | up |
| metallothionein 3 | Mt3 | chr8 | 2.0902364 | up |
| Nur77 downstream gene 2 | Ndg2 | chr10 | 2.0589802 | up |
| gasdermin domain containing 1 | Gsdmdc1 | chr15 | 1.9001833 | up |
| peroxisomal biogenesis factor 11a | Pex11a | chr7 | 1.8860891 | down |
| glutathione synthetase | Gss | chr2 | 1.8565459 | up |
| RIKEN cDNA 1810029B16 gene | 1810029B16Rik | chr8 | 1.8382206 | up |
| arginine vasopressin-induced 1 | Avpi1 | chr19 | 1.7936711 | up |
| Nur77 downstream gene 2 | Ndg2 | chr10 | 1.7673057 | up |
| interferon gamma inducible protein 30 | Ifi30 | chr8 | 1.7602197 | up |
| 0 day neonate skin cDNA, RIKEN full-length enriched library, clone: 4632424N07 product: unclassifiable, full insert sequence | | chr13 | 1.7456527 | up |
| 7 days embryo whole body cDNA, RIKEN full-length enriched library, clone: C430014D18 product: unclassifiable, full insert sequence | | chr1 | 1.6371719 | up |
| Rho family GTPase 1 | Rnd1 | chr15 | 1.6316801 | up |
| proviral integration site 3 | Pim3 | chr15 | 1.5919101 | up |
| transcription factor EC | Tcfec | chr6 | 1.5889215 | up |
| adenylate kinase 2 /// similar to adenylate kinase 2 | Ak2 /// LOC100047005 | chr4 | 1.5666348 | up |
| calreticulin 3 | Calr3 | chr8 | 1.5528721 | up |
| forkhead box P4 | Foxp4 | chr17 | 1.5294316 | up |

TABLE 2-continued

List of genes regulated by the IVVY (SEQ ID NO: 4) motif

| Gene Title | Gene Symbol | Chromosome Number | Fold Change | Up or Down |
|---|---|---|---|---|
| sulfiredoxin 1 homolog (*S. cerevisiae*) | Srxn1 | chr2 | 1.5259216 | up |
| lipoprotein lipase | Lpl | chr8 | 1.518442 | down |
| acyl-CoA synthetase long-chain family member 1 | Acsl1 | chr8 | 1.5109522 | up |
| peroxisome biogenesis factor 16 | Pex16 | chr2 | 1.5087851 | up |
| proviral integration site 3 | Pim3 | chr15 | 1.5076823 | up |
| Hypothetical protein LOC100042016 | LOC100042016 | chr11 | 1.5062494 | down |
| RIKEN cDNA 2810046L04 gene | 2810046L04Rik | chr3 | 1.502087 | down |
|  |  | chr11 | 1.5018126 | down |
| RIKEN cDNA 2810025M15 gene | 2810025M15Rik | chr1 | 1.4973557 | up |
| eukaryotic translation initiation factor 5A2 | Eif5a2 | chr3 | 1.496838 | down |
| HEAT repeat containing 1 | Heatr1 | chr13 | 1.496193 | down |
| EH-domain containing 1 | Ehd1 | chr19 | 1.4889908 | up |
| mitochondrial ribosomal protein L45 | Mrpl45 | chr11 | 1.4728131 | up |
| ubiquitin associated domain containing 2 | Ubac2 | chr14 | 1.4714627 | up |
| CDK2-associated protein 2 | Cdk2ap2 | chr19 | 1.4631894 | up |
| exosome component 1 | Exosc1 | chr19 | 1.459716 | down |
| RAB20, member RAS oncogene family | Rab20 | chr8 | 1.456158 | up |
| annexin A4 | Anxa4 | chr6 | 1.4501132 | up |
| EH-domain containing 1 | Ehd1 | chr19 | 1.4483279 | up |
| CTD (carboxy-terminal domain, RNA polymerase II, polypeptide A) small phosphatase like 2 | Ctdspl2 | chr2 | 1.4445461 | down |
| RIKEN cDNA 2400009B08 gene | 2400009B08Rik | chr8 | 1.4394982 | up |
| RIKEN cDNA 2810002O09 gene | 2810002O09Rik | chrX | 1.4358203 | up |
| 0 day neonate cerebellum cDNA, RIKEN full-length enriched library, clone: C230031C13 product: unclassifiable, full insert sequence |  | chr13 | 1.4317822 | down |
| chromodomain protein, Y chromosome-like 2 | Cdyl2 | chr8 | 1.429501 | up |
| Tnf receptor-associated factor 2 | Traf2 | chr2 | 1.4162527 | up |
| 12 days embryo male wolffian duct includes surrounding region cDNA, RIKEN full-length enriched library, clone: 6720430M22 product: unclassifiable, full insert sequence |  | chr14 | 1.4105098 | down |
| DENN/MADD domain containing 2D | Dennd2d | chr3 | 1.404753 | down |
| zinc finger protein 28 | Zfp28 | chr7 | 1.4026449 | down |
| death inducer-obliterator 1 | Dido1 | chr2 | 1.3924606 | up |
| golgi associated, gamma adaptin ear containing, ARF binding protein 2 | Gga2 | chr7 | 1.3818957 | up |
| Transcribed locus |  | chr4 | 1.3627918 | up |
| Cd99 antigen-like 2 | Cd99l2 | chrX | 1.3593745 | up |
| acyl-Coenzyme A dehydrogenase family, member 11 | Acad11 | chr9 | 1.3416152 | up |
| transmembrane protein 30A | Tmem30a | chr9 | 1.3382797 | down |
| paired-Ig-like receptor A1 /// paired-Ig-like receptor A11 /// paired- | Lilrb3 /// LOC100038908 /// | chr7 | 1.3368992 | up |
| zinc finger CCCH type containing 12C | Zc3h12c | chr9 | 1.2695061 | up |
| nuclear factor of kappa light chain gene enhancer in B-cells inhibitor, alpha | Nfkbia | chr12 | 1.2683418 | up |
| PR domain containing 2, with ZNF domain | Prdm2 | chr4 | 1.2645257 | up |
| eukaryotic translation initiation factor 4E binding protein 1 | Eif4ebp1 | chr8 | 1.2629627 | up |
| RIKEN cDNA 1110003F05 gene | 1110003F05Rik | chr17 | 1.2587925 | down |
| RIKEN cDNA D230040J21 gene | D230040J21Rik | chr5 | 1.2540071 | down |
| kelch-like 7 (*Drosophila*) | Klhl7 | chr5 | 1.2528863 | down |
| solute carrier family 25 (mitochondrial carrier, adenine nucleotide translocator), member 4 | Slc25a4 | chr8 | 1.2489876 | up |
| RIKEN cDNA B230337E12 gene | B230337E12Rik | chr1 | 1.2462453 | down |
| LEM domain containing 3 /// similar to LEM domain containing 3 | Lemd3 /// LOC100044466 | chr10 | 1.2456872 | down |
| steroid 5 alpha-reductase 2-like /// hypothetical protein LOC100044230 | LOC100044230 /// Srd5a2l | chr5 | 1.2416695 | up |
| RIKEN cDNA 6330416G13 gene | 6330416G13Rik | chr4 | 1.2402455 | up |
| GLE1 RNA export mediator-like (yeast) | Gle1l | chr2 | 1.2331597 | down |
| solute carrier family 25, member 39 | Slc25a39 | chr11 | 1.2330384 | up |
| ATPase, H+ transporting, lysosomal V0 subunit C /// similar to vacuolar H(+)-ATPase | Atp6v0c /// LOC100039636 /// LOC100046757 | chr6 | 1.2311169 | up |
| ATPase, H+ transporting, lysosomal V0 subunit B | Atp6v0b | chr4 | 1.2288831 | up |
| sorcin | Sri | chr5 | 1.2287564 | up |
| cyclin H | Ccnh | chr13 | 1.2249198 | down |
| ubiquitin-conjugating enzyme E2D 2 | Ube2d2 | chr18 | 1.2231128 | down |
| splicing factor, arginine/serine-rich 6 | Sfrs6 | chr2 | 1.2213966 | down |
| mitofusin 1 | Mfn1 | chr3 | 1.2205157 | up |
| 3-oxoacyl-ACP synthase, mitochondrial | Oxsm | chr14 | 1.2186738 | up |
| negative regulator of ubiquitin-like proteins 1 | Nub1 | chr5 | 1.2164594 | up |
| Vcell division cycle 73, Paf1/RNA polymerase II complex component, homolog (*S. cerevisiae*) | Cdc73 | chr1 | 1.215644 | down |
| peptidyl-prolyl isomerase G (cyclophilin G) | Ppig | chr2 | 1.2147061 | down |
| SUMO1 activating enzyme subunit 2 | Sae2 | chr7 | 1.2131295 | down |

TABLE 2-continued

List of genes regulated by the IVVY (SEQ ID NO: 4) motif

| Gene Title | Gene Symbol | Chromosome Number | Fold Change | Up or Down |
|---|---|---|---|---|
| eukaryotic translation initiation factor 4E binding protein 1 | Eif4ebp1 | chr8 | 1.2103645 | up |
| intraflagellar transport 20 homolog (*Chlamydomonas*) | Ift20 | chr11 | 1.2086008 | down |
| ATPase, H+ transporting, lysosomal V0 subunit B | Atp6v0b | chr4 | 1.2080344 | up |
| transmembrane BAX inhibitor motif containing 4 | Tmbim4 | chr10 | 1.2065625 | up |
| translocase of outer mitochondrial membrane 70 homolog A (yeast) | Tomm70a | chr16 | 1.2040935 | up |
| coiled-coil domain containing 93 | Ccdc93 | chr1 | 1.2035478 | up |
| RIKEN cDNA 2610301B20 gene | 2610301B20Rik | chr4 | 1.1994959 | down |
| isocitrate dehydrogenase 3 (NAD+) beta | Idh3b | chr2 | 1.1974369 | up |
| ATP synthase, H+ transporting, mitochondrial F0 complex, subunit c (subunit 9), isoform 3 | Atp5g3 | chr2 | 1.1937019 | up |
| RIKEN cDNA 1810013D10 gene | 1810013D10Rik | chr5 | 1.1921476 | up |
| translocase of outer mitochondrial membrane 20 homolog (yeast) | Tomm20 | chr2 | 1.190947 | up |
| zinc finger and BTB domain containing 48 | Zbtb48 | chr4 | 1.19065 | down |
| Ewing's tumor-associated antigen 1 | Etaa1 | chr11 | 1.1876866 | down |
| dynein light chain LC8-type 2 | Dynll2 | chr11 | 1.185562 | down |
| tripartite motif protein 23 | Trim23 | chr13 | 1.1853576 | down |
| splicing factor, arginine/serine-rich 2, interacting protein | Sfrs2ip | chr15 | 1.1847556 | down |
| solute carrier family 25 (mitochondrial carnitine/acylcarnitine translocase), member 20 | Slc25a20 | chr9 | 1.18337 | up |
| ankyrin repeat and zinc finger domain containing 1 | Ankzf1 | chr1 | 1.1801457 | down |
| RIKEN cDNA C330006K01 gene | C330006K01Rik | chr5 | 1.1782492 | up |
| RIKEN cDNA 2310035K24 gene | 2310035K24Rik | chr2 | 1.1772768 | up |
| mitochondrial ribosomal protein L9 | Mrpl9 | chr3 | 1.1764377 | up |
| RIKEN cDNA 1600012H06 gene | 1600012H06Rik | chr17 | 1.1758627 | down |
| BCL2-antagonist/killer 1 | Bak1 | chr17 | 1.1748867 | up |
| RIKEN cDNA 1200011O22 gene | 1200011O22Rik |  | 1.1721143 | up |
| squamous cell carcinoma antigen recognized by T-cells 1 | Sart1 | chr19 | 1.172027 | down |
| leucyl-tRNA synthetase | Lars | chr18 | 1.171722 | down |
| eukaryotic translation initiation factor 4, gamma 2 | Eif4g2 | chr7 | 1.1678882 | down |
| S-phase kinase-associated protein 1A | Skp1a | chr11 | 1.1656432 | up |
| glycerol phosphate dehydrogenase 2, mitochondrial | Gpd2 | chr2 | 1.1632929 | down |
| vav 1 oncogene | Vav1 | chr17 | 1.1601086 | down |
| APAF1 interacting protein /// similar to MMRP19 | Apip /// LOC100044135 | chr2 | 1.1600349 | up |
| splicing factor, arginine/serine-rich 6 | Sfrs6 | chr2 | 1.158874 | down |
| 10 days neonate cortex cDNA, RIKEN full-length enriched library, clone: A830030M19 product: unclassifiable, full insert sequence |  | chr3 | 1.1568067 | down |
| RAB22A, member RAS oncogene family | Rab22a | chr2 | 1.1567866 | up |
| mitochondrial ribosomal protein S14 | Mrps14 | chr1 | 1.1528465 | down |
| synaptophysin-like protein | Sypl | chr12 | 1.1516387 | down |
| AT hook containing transcription factor 1 | Ahctf1 | chr1 | 1.1466129 | up |
| suppressor of hairy wing homolog 3 (*Drosophila*) | Suhw3 | chrX | 1.1445446 | down |
| ring finger protein (C3H2C3 type) 6 | Rnf6 | chr5 | 1.1389387 | up |
| heterogeneous nuclear ribonucleoprotein K | Hnrpk | chr13 | 1.1362003 | down |
| DnaJ (Hsp40) homolog, subfamily C, member 14 | Dnajc14 | chr10 | 1.1335106 | up |
| Transcribed locus |  | chr19 | 1.1277171 | down |
| ERO1-like beta (*S. cerevisiae*) | Ero1lb | chr13 | 1.1264199 | down |
| transmembrane protein 18 | Tmem18 | chr12 | 1.125084 | down |
| dynein cytoplasmic 2 light intermediate chain 1 /// similar to Dynein cytoplasmic 2 light intermediate chain 1 | Dync2li1 /// LOC100048514 | chr17 | 1.1209211 | up |
| G1 to S phase transition 1 | Gspt1 | chr16 | 1.1209048 | down |
| actin related protein 2/3 complex, subunit 1A | Arpc1a | chr5 | 1.120718 | up |
| Rab9 effector protein with kelch motifs | Rabepk | chr2 | 1.1180472 | up |
| ubiquitin-conjugating enzyme E2 variant 1 | Ube2v1 | chr3 | 1.1133846 | up |
| DnaJ (Hsp40) homolog, subfamily B, member 4 | Dnajb4 | chr3 | 1.11245 | down |
| mitochondrial ribosomal protein L50 | Mrpl50 | chr4 | 1.1107732 | down |
| myoneurin | Mynn | chr3 | 1.1068301 | down |
| mitochondrial ribosomal protein L48 | Mrpl48 | chr4 | 1.1060202 | up |

Notably, a number of known osteoclast-related genes such as matrix metallopeptidase 9 (Mmp9), carbonic anhydrase 2 (Car2), cathepsin K (Ctsk) and tartrate resistant acid phosphatase 5 (Acp5/TRAP) were up-regulated more than 10 fold by the IVVY (SEQ ID NO:4) motif. RT-PCR analysis confirmed that the IVVY (SEQ ID NO:4) motif is involved in the transcriptional activation of Mmp9, Car2, Ctsk and TRAP genes (FIG. 5C). It was shown that the IVVY (SEQ ID NO:4) motif plays a crucial role in committing BMMs into the osteoclast lineage and it takes only 24 hours for the IVVY (SEQ ID NO:4) motif to fully commit BMMs into the osteoclast lineage (Xu et al., 2006). Moreover, once cells are fully committed by the IVVY (SEQ ID NO:4) motif, the TRAF-dependent signaling pathways are sufficient to mediate the remaining osteoclastogenic process.

Figure 5D:
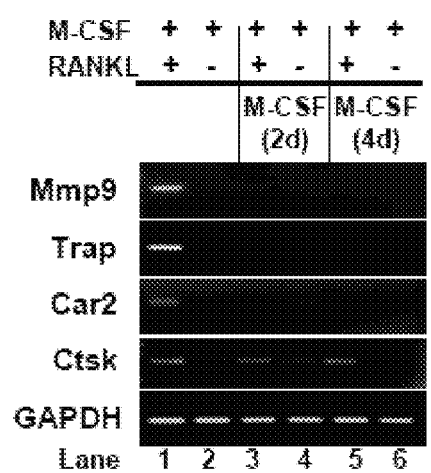
FIG. 5 illustrates that the IVVY (SEQ ID NO:4) motif regulates gene expression in response to RANKL treatment. (A) Heat map of microarray assays. BMMs isolated from TNFR1−/−2−/− mice were infected with virus encoding a chimeric receptor consisting of the TNFR external domain linked to the transmembrane and intracellular domains of mouse wild-type RANK (WT) or virus encoding a chimeric receptor consisting of the TNFR external domain linked to the transmembrane and intracellular domains of mouse RANK containing inactivating mutation in the IVVY (SEQ ID NO:4) motif (Mu). Infected cells were treated with M-CSF (44 ng/ml) and TNF (10 ng/ml) for 1d. Total RNA was isolated from the treated cells for microarray analysis. (B) Statistical analysis of the data obtained from the microarray assays. (C) The confirmation of data on the up-regulation of the Mmp9, Car2, Ctsk and TRAP genes by the IVVY (SEQ ID NO:4) motif using semi-quantitative RT-PCR. TNFR1−/−2−/− BMMs expressing the wild-type chimera (WT) and mutant chimera (Mu) were treated with M-CSF (44 ng/ml) and TNF-α (10 ng/ml) for 1d. Cells were lysed for total RNA isolation immediately after the 1d RANKL treatment or continued with M-CSF (44 ng/ml) alone for 2 or 4 additional days before total RNA preparation for semi-quantitative RT-PCR assessment of the expression of the four genes. (D) BMMs were treated with M-CSF (44 ng/ml) and RANKL (100 ng/ml) for 1d. As in (C), cells were either lysed for total RNA isolation immediately after the 1d RANKL treatment or continued with M-CSF (44 ng/ml) alone for 2 or 4 additional days before total RNA preparation for semiquantitative RT-PCR assessment of the expression of the four genes.

These data suggest that the IVVY (SEQ ID NO:4) motif can permanently activate some of its target genes. To investigate this possibility, BMMs were treated for 24 hours and the transcriptional activation of the Mmp9, Car2, Ctsk and TRAP genes was assessed by RT-PCR immediately, 2 days or 4 days after the 24-hour RANKL treatment (FIG. 5D). The data indicate that while the levels of the Mmp9, Car2 and TRAP mRNA decline 2 days after the 24-hour RANKL treatment, the RANKL-induced increase in the Ctsk mRNA levels persist 4 days after the RANKL treatment, suggesting that the RANKL-mediated activation of the Ctsk gene is permanent.

Shortly after the discovery of the RANKL/RANK system in the late 1990s, it was reported that RANK, upon binding by RANKL, activates a unique pathway(s) that distinguish itself from other members of the TNFR to regulate osteoclastogenesis (Yeh et al., 1999). This report was re-enforced by the recent identification of a novel RANK cytoplasmic motif which plays a crucial role in osteoclast lineage commitment (Xu et al., 2006). In the current studies, the long-sought RANK signaling pathway in osteoclastogenesis were elucidated to deal with two important issues: a) whether the IVVY (SEQ ID NO:4) motif mediates the osteoclast lineage commitment by recruiting an intracellular protein to activate a novel signaling pathway and b) whether the IVVY (SEQ ID NO:4) motif induces cell differentiation by regulating gene expression. These studies have revealed that the IVVY (SEQ ID NO:4) motif plays a critical role in osteoclastogenesis by interacting with RYBP, a protein interacting with members of the PcG family and various transcription factors including YY1 (Garcia et al., 1999), members of the E2F family (Trimarchi et al., 2001; Schlisio et al., 2002), E4TF1/hGABP (Sawa et al., 2002) and ubiquitinated H2A (Arrigoni et al., 2006), which is associated with transcriptional repression (Li et al., 2007). Moreover, specific RYBP domains involved in interacting with the RANK IVVY (SEQ ID NO:4) motif were identified. Furthermore, the data have also demonstrated that the IVVY (SEQ ID NO:4) motif/RYBP, or fragments thereof, regulates osteoclastogenesis via the activation of a large number of genes.

Osteoclasts play a pivotal role in both skeletal development and adult skeletal maintenance. During bone development, osteoclasts are required to degrade the cartilage matrix for vascular invasion in endochondral ossification (Lee and Einhorn, 2001). Furthermore, osteoclasts are also involved in bone growth and shape modification in endochondral ossification (bone modeling) (Baron, 2003). After skeletal maturation, osteoclasts continue to play a critical role in bone maintenance by participating in bone remodeling. Bone remodeling is a lifelong process of bone renewal in which old bone is resorbed by osteoclasts and then replaced by new bone formed by osteoblasts (Martin and Rodan, 2001). The constant remodeling of bone is required not only for maintaining healthy skeleton but also for regulating calcium homeostasis (Martin and Rodan, 2001).

Nonetheless, aberration in osteoclast formation and activity resulting in elevated bone resorption is implicated in the pathogenesis of postmenopausal osteoporosis (Teitelbaum, 2000), causes bone erosion in various inflammatory conditions including RA (Goldring, 2003), and plays a role in breast tumor bone metastasis (Mundy, 2002). Consequently, effective inhibition of osteoclast formation and activity has long been regarded as an attractive strategy for preventing and treating these bone diseases. However, currently available antiresorptive therapeutic agents such as estrogen, selective estrogen receptor modulators (SERMs), bisphosphonates and calcitonin either lack satisfactory efficacy or have potential to cause serious side effects in clinical management of postmenopausal osteoporosis and bone loss associated with other pathological conditions (Stepan et al., 2003; Lufkin et al., 2004; Marcus et al., 2002). Thus, development of new antiresorptive therapeutic drugs with higher potency and specificity is imperative.

The discovery of RANKL and its two receptors RANK and osteoprotegerin (OPG) in the late 1990's has created huge enthusiasm for developing new antiresorptive agents targeting the RANKL/RANK/OPG regulatory axis. So far, efforts have been undertaken in developing OPG, soluble RANK-Fc, and anti-RANKL antibodies as new antiresorptive therapeutics to treat bone diseases (Doggrell, 2003; Zhang et al., 2003; Bekker et al., 2004). However, all of these agents have an inherited drawback as therapeutic drugs, primarily due to the fact that their action lacks specificity. The RANKL/RANK system is not only involved in osteoclast formation and function (Hsu et al., 1999), but is also a critical mediator of other biological processes such as dendritic cell (DC) survival and activation (Wong et al., 1997a; Josien et al., 1999; Josien et al., 2000), Tcell activation (Kong et al., 1999; Bachmann et al., 1999), lymph node organogenesis (Kong et al., 1999; Dougall et al., 1999; Kim et al., 2000a), B-cell differentiation (Kong et al., 1999; Dougall et al., 1999), mammary gland development (Fata et al., 2000), and thermoregulation in females or fever response inflammation (Hanada et al., 2009).

The RANK IVVY (SEQ ID NO:4) motif/RYBP, or fragments thereof, pathway represents a new antiresorptive drug target for the following three reasons. First, the IVVY (SEQ ID NO:4) motif/RYBP pathway plays an essential role in osteoclastogenesis (Xu et al., 2006) (FIG. 3). As a result, therapeutic blockage of this new signaling pathway in osteoclast precursors would result in a dramatic reduction in osteoclastogenesis. Secondly, the IVVY (SEQ ID NO:4) motif/RYBP pathway also represents a specific antiresorptive target for treating bone diseases involving osteoclasts. It has been well established that TNF family members play crucial roles in various immune functions primarily by engaging TRAF proteins (Arron et al., 2002; Xie et al., 2008) (Kobayashi et al., 2003). However, the IVVY (SEQ ID NO:4) motif recruits RYBP to activate a TRAF-independent pathway. As such, therapeutic targeting of the IVVY (SEQ ID NO:4)/RYBP pathway should have minimal effect on immune response and associated side effects. Moreover, the specific RYBP domains identified which mediate interaction with the RANK IVVY (SEQ ID NO:4) motif provide potential therapeutic candidates and targets and/or facilitate development of either biochemical or cell-based assays for identifying small molecules targeting the interaction between the IVVY (SEQ ID NO:4) motif and RYBP protein.

References

Amarzguioui, M., Holen, T., Babaie, E., and Prydz, H. (2003). Tolerance for mutations and chemical modifications in a siRNA. Nucleic Acids Research 31, 589-595.

Anderson, D. M., Maraskovsky, E., Billingsley, W. L., Dougall, W. C., Tometsko, M. E., Roux, E. R., Teepe, M. C., DuBose, R. F., Cosman, D., and Galibert, L. (1997). A homologue of the TNF receptor and its ligand enhance T-cell growth and dendritic-cell function. Nature 390, 175-179.

Arrigoni, R., Alam, S. L., Wamstad, J. A., Bardwell, V. J., Sundquist, W. I., and Schreiber-Agus, N. (2006). The Polycomb-associated protein Rybp is a ubiquitin binding protein. FEBS Lett. 580, 6233-6241.

Arron, J. R., Walsh, M. C., and Choi, Y. (2002). TRAF-mediated TNFR-family signaling. Cum Protoc. Immunol. Chapter 11, Unit.

Azuma, Y., Kaji, K., Katogi, R., Takeshita, S., and Kudo, A. (2000). Tumor necrosis factor-alpha induces differentiation of and bone resorption by osteoclasts. J. Biol. Chem. 275, 4858-4864.

Bachmann, M. F., Wong, B. R., Josien, R., Steinman, R. M., Oxenius, A., and Choi, Y. (1999). TRANCE, a tumor necrosis factor family member critical for CD40 ligand-independent T helper cell activation. J. Exp. Med. 189, 1025-1031.

Baron, R. (2003). General principle of bone biology. In Primer on the metabolic bone diseases and disorders of mineral metabolism, M. J. Favus, ed. (Washington D. C.: ASBMR), pp. 1-8.

Bekker, P. J., Holloway, D. L., Rasmussen, A. S., Murphy, R., Martin, S. W., Leese, P. T., Holmes, G. B., Dunstan, C. R., and DePaoli, A. M. (2004). A single-dose placebo-controlled study of AMG 162, a fully human monoclonal antibody to RANKL, in postmenopausal women. J. Bone Miner. Res. 19, 1059-1066.

Boyle, W. J., Simonet, W. S., and Lacey, D. L. (2003). Osteoclast differentiation and activation. [Review] [77 refs]. Nature 423, 337-342.

Bucay, N., Sarosi, I., Dunstan, C. R., Morony, S., Tarpley, J., Capparelli, C., Scully, S., Tan, H. L., Xu, W., Lacey, D. L., Boyle, W. J., and Simonet, W. S. (1998). osteoprotegerin-deficient mice develop early onset osteoporosis and arterial calcification. Genes Dev. 12, 1260-1268.

Cao, R. and Zhang, Y. (2004). The functions of E(Z)/EZH2-mediated methylation of lysine 27 in histone H3. Curr. Opin. Genet. Dev. 14,155-164.

Chen, D., Zhang, J., Li, M., Rayburn, E. R., Wang, H., and Zhang, R. (2009). RYBP stabilizes p53 by modulating MDM2. EMBO Rep. 10, 166-172.

Chung, J. Y., Park, Y. C., Ye, H., and Wu, H. (2002). All TRAFs are not created equal: common and distinct molecular mechanisms of TRAF-mediated signal transduction. [Review] [124 refs]. J. Cell Sci. 115, 679-688.

Danen-van Oorschot, A. A., Voskamp, P., Seelen, M. C., van Miltenburg, M. H., Bolk, M. W., Tait, S. W., Boesen-de Cock, J. G., Rohn, J. L., Borst, J., and Noteborn, M. H. (2004). Human death effector domain-associated factor interacts with the viral apoptosis agonist Apoptin and exerts tumor-preferential cell killing. Cell Death. Differ. 11, 564-573.

Darnay, B. G., Haridas, V., Ni, J., Moore, P. A., and Aggarwal, B. B. (1998). Characterization of the intracellular domain of receptor activator of NF-kappaB (RANK). Interaction with tumor necrosis factor receptor-associated factors and activation of NF-kappab and c-Jun N-terminal kinase. J. Biol. Chem. 273, 20551-20555.

Darnay, B. G., Ni, J., Moore, P. A., and Aggarwal, B. B. (1999). Activation of NF-kappaB by RANK requires tumor necrosis factor receptor-associated factor (TRAF) 6 and NF-kappaB-inducing kinase. Identification of a novel TRAF6 interaction motif. J. Biol. Chem. 274, 7724-7731.

Doggrell, S. A. (2003). Present and future pharmacotherapy for osteoporosis. [Review] [155 refs]. Drugs of Today 39, 633-657.

Dougall, W. C., Glaccum, M., Charrier, K., Rohrbach, K., Brasel, K., De Smedt, T., Daro, E., Smith, J., Tometsko, M. E., Maliszewski, C. R., Armstrong, A., Shen, V., Bain, S., Cosman, D., Anderson, D., Morrissey, P. J., Peschon, J. J., Schuh, and J. (1999). RANK is essential for osteoclast and lymph node development. Genes Dev. 13, 2412-2424.

Fata, J. E., Kong, Y. Y., Li, J., Sasaki, T., Irie-Sasaki, J., Moorehead, R. A., Elliott, R., Scully, S., Voura, E. B., Khokha, R., and Penninger, J. M. (2000). The osteoclast differentiation factor osteoprotegerin-ligand is essential for mammary gland development. Cell 103, 41-50.

Feng, X. (2005). Regulatory roles and molecular signaling of TNF family members in osteoclasts. [Review] [133 refs]. Gene 350, 1-13.

Feng, X., Novack, D. V., Faccio, R., Ory, D. S., Aya, K., Boyer, M. I., McHugh, K. P., Ross, F. P., and Teitelbaum, S. L. (2001). A Glanzmann's mutation in beta 3 integrin specifically impairs osteoclast function. J. Clin. Invest. 107, 1137-1144.

Galibert, L., Tometsko, M. E., Anderson, D. M., Cosman, D., Dougall, and WC. (1998). The involvement of multiple tumor necrosis factor receptor (TNFR)-associated factors in the signaling mechanisms of receptor activator of NF-kappaB, a member of the TNFR superfamily. J. Biol. Chem. 273, 34120-34127.

Garcia, E., Marcos-Gutierrez, C., del Mar, L. M., Moreno, J. C., and Vidal, M. (1999). RYBP, a new repressor protein that interacts with components of the mammalian Polycomb complex, and with the transcription factor YY1. EMBO J. 18, 3404-3418.

Gecz, J., Gaunt, S. J., Passage, E., Burton, R. D., Cudrey, C., Pearce, J. J., and Fontes, M. (1995). Assignment of a Polycomb-like chromobox gene (CBX2) to human chromosome 17q25. Genomics 26, 130-133.

Goldring, S. R. (2003). Pathogenesis of bone and cartilage destruction in rheumatoid arthritis. [Review] [48 refs]. Rheumatology 42 Suppl 2, ii11-ii16.

Gonzalez, I., Aparicio, R., and Busturia, A. (2008). Functional characterization of the dRYBP gene in Drosophila. Genetics 179, 1373-1388.

Hall, J. (2004). Opinion: Unravelling the general properties of siRNAs: strength in numbers and lessons from the past. [Review] [59 refs]. Nature Reviews Genetics 5, 552-557.

Hanada, R., Leibbrandt, A., Hanada, T., Kitaoka, S., Furuyashiki, T., Fujihara, H., Trichereau, J., Paolino, M., Qadri, F., Plehm, R., Klaere, S., Komnenovic, V., Mimata, H., Yoshimatsu, H., Takahashi, N., von Haeseler, A., Bader, M., Kilic, S. S., Ueta, Y., Pifl, C., Narumiya, S., and Penninger, J. M. (2009). Central control of fever and female body temperature by RANKL/RANK. Nature 462, 505-509.

Hsu, H., Lacey, D. L., Dunstan, C. R., Solovyev, I., Colombero, A., Timms, E., Tan, H.-L., Elliott, G., Kelley, M. J., Sarosi, I., Wang, L., Xia, X. Z., Elliott, R., Chiu, L., Black, T., Scully, S., Capparelli, C., Morony, S., Shimamoto, G., Bass, M. B., and Boyle, W. J. (1999). Tumor necrosis factor receptor family member RANK mediates osteoclast differentiation and activation induced by osteoprotegerin ligand. Proc. Natl. Acad. Sci. U.S.A. 96, 3540-3545.

Josien, R., Li, H. L., Ingulli, E., Sarma, S., Wong, B. R., Vologodskaia, M., Steinman, R. M., and Choi, Y. (2000). TRANCE, a tumor necrosis factor family member, enhances the longevity and adjuvant properties of dendritic cells in vivo. J. Exp. Med. 191, 495-502.

Josien, R., Wong, B. R., Li, H. L., Steinman, R. M., and Choi, Y. (1999). TRANCE, a TNF family member, is differentially expressed on T cell subsets and induces cytokine production in dendritic cells. J. Immunol. 162, 2562-2568.

Kim, D., Mebius, R. E., MacMicking, J. D., Jung, S., Cupedo, T., Castellanos, Y., Rho, J., Wong, B. R., Josien, R., Kim, N., Rennert, P. D., and Choi, Y. (2000a). Regulation of peripheral lymph node genesis by the tumor necrosis factor family member TRANCE. J. Exp. Med. 192, 1467-1478.

Kim, H. H., Lee, D. E., Shin, J. N., Lee, Y. S., Jeon, Y. M., Chung, C. H., Ni, J, Kwon, B. S., and Lee, Z. H. (1999).

Receptor activator of NF-kappaB recruits multiple TRAF family adaptors and activates c-Jun N-terminal kinase. FEBS Letters 443, 297-302.

Kim, N., Odgren, P. R., Kim, D. K., Marks, S. C., and Choi, Y. (2000b). Diverse roles of the tumor necrosis factor family member TRANCE in skeletal physiology revealed by TRANCE deficiency and partial rescue by a lymphocyte-expressed TRANCE transgene. Proc. Natl. Acad. Sci. U.S.A. 97, 10905-10910.

Kobayashi, K., Takahashi, N., Jimi, E., Udagawa, N., Takami, M., Kotake, S., Nakagawa, N., Kinosaki, M., Yamaguchi, K., Shima, N., Yasuda, H., Morinaga, T., Higashio, K., Martin, T. J., and Suda, T. (2000). Tumor necrosis factor alpha stimulates osteoclast differentiation by a mechanism independent of the ODF/RANKL-RANK interaction. J. Exp. Med. 191, 275-285.

Kobayashi, T., Walsh, P. T., Walsh, M. C., Speirs, K. M., Chiffoleau, E., King, C. G., Hancock, W. W., Caamano, J. H., Hunter, C. A., Scott, P., Turka, L. A., and Choi, Y. (2003). TRAF6 is a critical factor for dendritic cell maturation and development. Immunity 19, 353-363.

Kohler, C. and Villar, C. B. (2008). Programming of gene expression by Polycomb group proteins. Trends Cell Biol. 18, 236-243.

Kong, Y. Y., Yoshida, H., Sarosi, I., Tan, H. L., Timms, E., Capparelli, C., Morony, S., Oliveira, d.S. A., Van, G., Itie, A., Khoo, W., Wakeham, A., Dunstan, C. R., Lacey, D. L., Mak, T. W., Boyle, W. J., and Penninger, J. M. (1999). OPGL is a key regulator of osteoclastogenesis, lymphocyte development and lymph-node organogenesis. Nature 397, 315-323.

Lacey, D. L., Timms, E., Tan, H. L., Kelley, M. J., Dunstan, C. R., Burgess, T., Elliott, R., Colombero, A., Elliott, G., Scully, S., Hsu, H., Sullivan, J, Hawkins, N., Davy, E., Capparelli, C., Eli, A., Qian, Y. X., Kaufman, S., Sarosi, I, Shalhoub, V., Senaldi, G., Guo, J., Delaney, J., and Boyle, W. J. (1998). Osteoprotegerin ligand is a cytokine that regulates osteoclast differentiation and activation. Cell 93, 165-176.

Lam, J., Takeshita, S., Barker, J. E., Kanagawa, 0., Ross, F. P., and Teitelbaum, S. L. (2000). TNFalpha induces osteoclastogenesis by direct stimulation of macrophages exposed to permissive levels of RANK ligand. J. Clin. Invest. 106, 1481-1488.

Lee, C. A. and Einhorn, T. A. (2001). The bone organ system: Form and Function. In Osteoporosis, R., Marcus, D. Feldman, and J. Kelsey, eds. (San Diego: Academic Press), pp. 3-21.

Li, B., Carey, M., and Workman, J. L. (2007). The role of chromatin during transcription. Cell 128, 707-719.

Li, J., Sarosi, I., Yan, X.-Q., Morony, S., Capparelli, C., Tan, H.-L., McCabe, S., Elliott, R., Scully, S., Van, G., Kaufman, S., Juan, S.-C., Sun, Y., Tarpley, J., Martin, L., Christensen, K., McCabe, J., Kostenuik, P., Hsu, H., Fletcher, F., Dunstan, C. R., Lacey, D. L., and Boyle, W. J. (2000). RANK is the intrinsic hematopoietic cell surface receptor that controls osteoclastogenesis and regulation of bone mass and calcium metabolism. Proc. Natl. Acad. Sci. U.S.A. 97, 1566-1571.

Liu, W., Wang, S., Wei, S., Sun, L., and Feng, X. (2005). RANK cytoplasmic motif, PFQEP369-373, plays a predominant role in osteoclast survival in part by activating Akt/PKB and its downstream effector AFX/FOXO4. J. Biol. Chem 280, 43064-43072.

Liu, W., Xu, D., Yang, H., Xu, H., Shi, Z., Cao, X., Takeshita, S., Liu, J., Teale, M., and Feng, X. (2004). Functional identification of three RANK cytoplasmic motifs mediating osteoclast differentiation and function. J. Biol. Chem 279, 54759-54769.

Locksley, R. M., Killeen, N., and Lenardo, M. J. (2001). The TNF and TNF receptor superfamilies: integrating mammalian biology. [Review] [115 refs]. Cell 104, 487-501.

Lufkin, E. G., Sarkar, S., Kulkarni, P. M., Ciaccia, A. V., Siddhanti, S., Stock, J., and Plouffe, L., Jr. (2004). Antiresorptive treatment of postmenopausal osteoporosis: review of randomized clinical studies and rationale for the Evista alendronate comparison (EVA) trial. [Review] [48 refs]. Current Medical Research & Opinion 20, 351-357.

Marcus, R., Wong, M., Heath, H., III, and Stock, J. L. (2002). Antiresorptive treatment of postmenopausal osteoporosis: comparison of study designs and outcomes in large clinical trials with fracture as an endpoint. [Review] [149 refs]. Endocr. Revs. 23, 16-37.

Martin, T. J. and Rodan, G. A. (2001). Coupling of bone resorption and formation during bone remodeling. In Osteoporosis, R. Marcus, D. Feldman, and J. Kelsey, eds. (San Diego: Academic Press), pp. 361-372.

Mizuno, A., Amizuka, N., Irie, K., Murakami, A., Fujise, N., Kanno, T., Sato, Y., Nakagawa, N., Yasuda, H., Mochizuki, S., Gomibuchi, T., Yano, K., Shima, N., Washida, N., Tsuda, E., Morinaga, T., Higashio, K., and Ozawa, H. (1998). Severe osteoporosis in mice lacking osteoclastogenesis inhibitory factor/osteoprotegerin. Biochem. Biophys. Res. Commun. 247, 610-615.

Mundy, G. R. (2002). Metastasis to bone: causes, consequences and therapeutic opportunities. [Review] [76 refs]. Nature Reviews Cancer. 2, 584-593.

Ory, D. S., Neugeboren, B. A., and Mulligan, R. C. (1996). A stable human-derived packaging cell line for production of high titer retrovirus/vesicular stomatitis virus G pseudotypes. Proc. Natl. Acad. Sci. U.S.A. 93, 11400-11406.

Pirity, M. K., Locker, J., and Schreiber-Agus, N. (2005). Rybp/DEDAF is required for early postimplantation and for central nervous system development. Mol. Cell Biol. 25, 7193-7202.

Pusch, 0., Boden, D., Silbermann, R., Lee, F., Tucker, L., and Ramratnam, B. (2003). Nucleotide sequence homology requirements of HIV-1-specific short hairpin RNA. Nucleic Acids Research 31, 6444-6449.

Raisz, L. G. (2005). Pathogenesis of osteoporosis: concepts, conflicts, and prospects. J. Clin. Invest 115, 3318-3325.

Sawa, C., Yoshikawa, T., Matsuda-Suzuki, F., Delehouzee, S., Goto, M., Watanabe, H., Sawada, J., Kataoka, K., and Handa, H. (2002). YEAF1/RYBP and YAF-2 are functionally distinct members of a cofactor family for the YY1 and E4TF1/hGABP transcription factors. J. Biol. Chem. 277, 22484-22490.

Schlisio, S., Halperin, T., Vidal, M., and Nevins, J. R. (2002). Interaction of YY1 with E2Fs, mediated by RYBP, provides a mechanism for specificity of E2F function. EMBO J. 21, 5775-5786.

Schuettengruber, B., Chourrout, D., Vervoort, M., Leblanc, B., and Cavalli, G. (2007). Genome regulation by polycomb and trithorax proteins. Cell 128, 735-745.

Schwartz, Y. B. and Pirrotta, V. (2007). Polycomb silencing mechanisms and the management of genomic programmes. Nat. Rev. Genet. 8, 9-22.

Schwartz, Y. B. and Pirrotta, V. (2008). Polycomb complexes and epigenetic states. Curr. Opin. Cell Biol. 20, 266-273.

Simonet, W. S., Lacey, D. L., Dunstan, C. R., Kelley, M., Chang, M. S., Luthy, R., Nguyen, H. Q., Wooden, S., Bennett, L., Boone, T., Shimamoto, G., DeRose, M, Elliott, R., Colombero, A., Tan, H. L., Trail, G., Sullivan, J., Davy, E., Bucay, N, Renshaw-Gegg, L., Hughes, T. M., Hill, D., Pattison, W., Campbell, P., and Boyle, W. J. (1997). Osteoprotegerin: a novel secreted protein involved in the regulation of bone density. Cell 89, 309-319.

Stanton, S. E., Blanck, J. K., Locker, J., and Schreiber-Agus, N. (2007). Rybp interacts with Hippi and enhances Hippi-mediated apoptosis. Apoptosis. 12, 2197-2206.

Stepan, J. J., Alenfeld, F., Boivin, G., Feyen, J. H., and Lakatos, P. Mechanisms of action of antiresorptive therapies of postmenopausal osteoporosis. [Review] [59 refs] Source Endocrine Regulations. 37(4):225-38, 2003 December.

Suda, T., Takahashi, N., Udagawa, N., Jimi, E., Gillespie, M. T., and Martin, T. J. (1999). Modulation of osteoclast differentiation and function by the new members of the tumor necrosis factor receptor and ligand families. Endocr. Revs. 20, 345-357.

Takeshita, S., Kaji, K., and Kudo, A. (2000). Identification and characterization of the new osteoclast progenitor with macrophage phenotypes being able to differentiate into mature osteoclasts. J. Bone Miner. Res. 15, 1477-1488.

Teitelbaum, S. L. (2000). Bone resorption by osteoclasts. Science 289, 1504-1508.

Trimarchi, J. M., Fairchild, B., Wen, J., and Lees, J. A. (2001). The E2F6 transcription factor is a component of the mammalian Bmil-containing polycomb complex. Proc. Natl. Acad. Sci. U. S. A 98, 1519-1524.

Tsuda, E., Goto, M., Mochizuki, S., Yano, K., Kobayashi, F., Morinaga, T., and Higashio, K. (1997). Isolation of a novel cytokine from human fibroblasts that specifically inhibits osteoclastogenesis. Biochem. Biophys. Res. Commun. 234, 137-142.

Wong, B. R., Josien, R., Lee, S. Y., Sauter, B., Li, H. L., Steinman, R M, and Choi, Y. (1997a). TRANCE (tumor necrosis factor [TNF]-related activation-induced cytokine), a new TNF family member predominantly expressed in T cells, is a dendritic cell-specific survival factor. J. Exp. Med. 186, 2075-2080.

Wong, B. R., Josien, R., Lee, S. Y., Vologodskaia, M., Steinman, R. M., and Choi, Y. W. (1998). The TRAF family of signal transducers mediates NF-KAPPA-B activation by the TRANCE receptor. J. Biol. Chem. 273, 28355-28359.

Wong, B. R., Rho, J., Anon, J., Robinson, E., Orlinick, J., Chao, M, Kalachikov, S., Cayani, E., Bartlett, F. S., III, Frankel, W. N., Lee, S. Y., and Choi, Y. (1997b). TRANCE is a novel ligand of the tumor necrosis factor receptor family that activates c-Jun N-terminal kinase in T cells. J. Biol. Chem. 272, 25190-25194.

Wu, H. and Arron, J. R. (2003). TRAF6, a molecular bridge spanning adaptive immunity, innate immunity and osteoimmunology. BioEssays 25, 1096-1105.

Wu, Z., Irizarry, R. A., Gentleman, R., Martinez-Murillo, F., and Spencer, F. (2004). A model-based background adjustment for oligonucleotide expression arrays. Journal of the American Statistical Association 99, 909-917.

Xie, P., Kraus, Z. J., Stunz, L. L., and Bishop, G. A. (2008). Roles of TRAF molecules in B lymphocyte function. Cytokine Growth Factor Rev. 19, 199-207.

Xu, D., Wang, S., Liu, W., Liu, J., and Feng, X. (2006). A novel RANK cytoplasmic motif plays an essential role in osteoclastogenesis by committing macrophages to the osteoclast lineage. J. Biol. Chem 281, 4678-4690.

Yasuda, H., Shima, N., Nakagawa, N., Yamaguchi, K., Kinosaki, M., Mochizuki, S., Tomoyasu, A., Yano, K., Goto, M., Murakami, A., Tsuda, E., Morinaga, T., Higashio, K., Udagawa, N., Takahashi, N., and Suda, T. (1998). Osteoclast differentiation factor is a ligand for osteoprotegerin/osteoclastogenesis-inhibitory factor and is identical to TRANCE/RANKL. Proc. Natl. Acad. Sci. U.S.A. 95, 3597-3602.

Ye, H., Arron, J. R., Lamothe, B., Cirilli, M., Kobayashi, T., Shevde, N. K., Segal, D., Dzivenu, O. K., Vologodskaia, M., Yim, M., Du, K., Singh, S., Pike, J. W., Darnay, B. G., Choi, Y., and Wu, H. (2002). Distinct molecular mechanism for initiating TRAF6 signalling. Nature 418, 443-447.

Yeh, W. C., Hakem, R., Woo, M., and Mak, T. W. (1999). Gene targeting in the analysis of mammalian apoptosis and TNF receptor superfamily signaling. Immunological Reviews 169, 283-302.

Zhang, J., Dai, J., Yao, Z., Lu, Y., Dougall, W., and Keller, E. T. (2003). Soluble receptor activator of nuclear factor kappaB Fc diminishes prostate cancer progression in bone. Cancer Res 63,7883-7890.

Zheng, L., Schickling, O., Peter, M. E., and Lenardo, M. J. (2001). The death effector domainassociated factor plays distinct regulatory roles in the nucleus and cytoplasm. J. Biol. Chem. 276, 31945-31952.

What is claimed is:

1. An isolated RYBP peptide selected from an amino acid sequence as set forth in SEQ ID NO:3, an amino acid sequence at least 90% identical to SEQ ID NO:3, or a fragment thereof, wherein said RYBP peptide specifically interacts with a RANK peptide comprising amino acid sequence IVVY (SEQ ID NO:4).

2. The RYBP peptide of claim 1, wherein the peptide comprises the amino acid sequence VIIT (SEQ ID NO:5).

3. The RYBP peptide of claim 1, wherein the peptide comprises the amino acid sequence AVTV (SEQ ID NO:6).

4. The RYBP peptide of claim 1, consisting of the amino acid sequence of SEQ ID NO:3.

5. The RYBP peptide of claim 1, wherein the peptide comprises the amino acid sequence VIIT (SEQ ID NO:5) and AVTV (SEQ ID NO:6).

6. A composition comprising a pharmaceutically acceptable excipient and the RYBP peptide of claim 1.

7. The composition of claim 6, wherein the RYBP peptide consists of the amino acid sequence of SEQ ID NO:3.

8. The composition of claim 6, wherein the RYBP peptide comprises the amino acid sequence VIIT (SEQ ID NO:5).

9. The composition of claim 6, wherein the RYBP peptide comprises the amino acid sequence AVTV (SEQ ID NO:6).

10. The composition of claim 6, wherein the RYBP peptide comprises the amino acid sequence VIIT (SEQ ID NO:5) and AVTV (SEQ ID NO:6).

* * * * *

SEQUENCE LISTING

```
<160> NUMBER OF SEQ ID NOS: 29

<210> SEQ ID NO 1
<211> LENGTH: 4472
<212> TYPE: DNA
<213> ORGANISM: Mus sp.
<220> FEATURE:
<221> NAME/KEY: CDS
<222> LOCATION: (165)..(848)

<400> SEQUENCE: 1
ggcggcggca gcggcggcgg cggcggcggc tggagctcga gcccagcagc ggagggcggg      60
cgggcggcgc gggagggcgg gggccgctcc gcgacgctgc ggaccgcgct tctcctctga     120
gcggcggcgc gcgcagctgt ggggcgccgg gggccagccc gtcc atg acc atg ggc     176
                                                Met Thr Met Gly
                                                  1 gac aag aag agc ccg acc agg cca aaa aga caa gcg aaa cct gcc gca     224
Asp Lys Lys Ser Pro Thr Arg Pro Lys Arg Gln Ala Lys Pro Ala Ala
  5                  10                  15                  20
```

```
gac gaa ggc ttt tgg gat tgt agc gtc tgc acc ttt agg aac agc gcc      272
Asp Glu Gly Phe Trp Asp Cys Ser Val Cys Thr Phe Arg Asn Ser Ala
                25                  30                  35 gaa gcc ttt aaa tgc agc atc tgc gat gtg cgg aaa ggc acc tcc acc      320
Glu Ala Phe Lys Cys Ser Ile Cys Asp Val Arg Lys Gly Thr Ser Thr
            40                  45                  50 agg aaa cct cgc atc aat tct cag ctg gtg gca cag cag gtg gca cag      368
Arg Lys Pro Arg Ile Asn Ser Gln Leu Val Ala Gln Gln Val Ala Gln
        55                  60                  65 cag tac gcc act cca cct ccc cct aag aag gag aag aag gag aag gtc      416
Gln Tyr Ala Thr Pro Pro Pro Pro Lys Lys Glu Lys Lys Glu Lys Val
    70                  75                  80 gaa aag cct gac aaa gaa aag cca gag aaa gac aag gac att agc ccc      464
Glu Lys Pro Asp Lys Glu Lys Pro Glu Lys Asp Lys Asp Ile Ser Pro
85                  90                  95                 100 agt gtc acc aag aaa aac acc aac aag aaa aca aaa cca aag tct gat      512
Ser Val Thr Lys Lys Asn Thr Asn Lys Lys Thr Lys Pro Lys Ser Asp
                105                 110                 115 att ctg aaa gat cct cct agt gaa gct aac agc ata cag tct gct aac      560
Ile Leu Lys Asp Pro Pro Ser Glu Ala Asn Ser Ile Gln Ser Ala Asn
            120                 125                 130 gct aca aca aag acc agc gaa aca aac cac acc tca agg ccc cgg ctg      608
Ala Thr Thr Lys Thr Ser Glu Thr Asn His Thr Ser Arg Pro Arg Leu
        135                 140                 145 aag aat gtg gac agg agc acc gca cag cag ttg gca gta act gtg ggc      656
Lys Asn Val Asp Arg Ser Thr Ala Gln Gln Leu Ala Val Thr Val Gly
    150                 155                 160 aac gtc acc gtc att atc aca gac ttt aag gaa aag act cgc tcc tcc      704
Asn Val Thr Val Ile Ile Thr Asp Phe Lys Glu Lys Thr Arg Ser Ser
165                 170                 175                 180 tcc aca tcc tct tcc aca gtg acc tcc agt gca ggg tca gaa cag cag      752
Ser Thr Ser Ser Ser Thr Val Thr Ser Ser Ala Gly Ser Glu Gln Gln
                185                 190                 195 aac cag agc agc tcg ggc tca gag agc aca gac aaa ggc tcc tcc cgc      800
Asn Gln Ser Ser Ser Gly Ser Glu Ser Thr Asp Lys Gly Ser Ser Arg
            200                 205                 210 tcc tcc acg cca aag ggc gac atg tca gca gtg aat gat gaa tct ttc      848
Ser Ser Thr Pro Lys Gly Asp Met Ser Ala Val Asn Asp Glu Ser Phe
        215                 220                 225 tgagattgca catggaattg tgaaactatg aatcagggta tgagattcaa accctccacc     908
tgcccatgct gcttgcaccc tggagagtct tctgtggacg accttgtagt gacgctacca     968
ggagaggttc cgcttgccgt gggcatctgg ctaccaagga atttcgtacc ctgacagtta    1028
ctcttgacac ttttatgtat tccattgttt tatatgattt tcctaacaat catttataat    1088
tggatgtgcc cctgaatcta ctttttatat atatatataa aaaaaatctg ctgtgcacaa    1148
ttttccatgt acattacaac tggttttgtt tctgttttgt tgaagagggt tgggagggga    1208
gagggaactt ttatttattg tgttcacaga ctccatcctg tcagcatatc ctcttaaatt    1268
tagttctttc ttccagctat actctgtact atcagttttg ataactat atatataaat     1328 ataaaattat atataaaggg ttatttgaaa ccaatccatg gcaacgctgg tgcttgatac    1388
actgtgaagt gaatacaaca ttgaacagtt gacacagatc tgggacagtc ccttctatga    1448
aagtgctgaa atatcattaa aatcagtctt acatgaagta tgttccaacc tgcgtgggaa    1508
cttgactctc tcatctgtct ttagagtact ggataatata aaaatatat ttttaaaca     1568 atgtgatctc aaatttaaag actgctccag atagcctgca tttgcaatgg gctaattgac    1628
```

```
aaatgacaag tggttcagtt ggagggcttt gaccattcgg aagtaacaag actagctcca    1688
gaatgccaag tattcgtgta aattatggtt acatgttaac attgctgttt ttattaagca    1748
ctcatgagaa tatggtgttc tgtatctcga attccggcct ttttccagac ctctgctcac    1808
gcctgaggta tatctagcag ctgtcttagt tctaggggtg cggtagtgca tctttgaatc    1868
cacaccaccc agggaagcag tctacatcct ctgtggtgtt gcagtggtgg attttgtgat    1928
catggcctgt tttactcctc ctcccgtacc ccgtcctcca aatcctcacc ctaccaatgc    1988
agttgttagt cttcttct aaaacctact atggctcatt ttattaaaca agggttgtca    2048
acctcacatc cagacctgac acagagatct tccagtctct ggagtcagtt cttagttcct    2108
tgtgtgggaa aggatcgcag gggtgcatgg gcgagttgcg gggaaagctc acttcccagg    2168
agagtgaatg aatagtaggt gttctttgtt gactgaactc ttgaaagctt ttcattttca    2228 ccatttagg ggtaggagat aatgaaagac cactgataat agtttatcat cccatcccaa    2288
gtctcagtga ctctgctttg ctcttagatt cagggtatct ctcctatctg acttagcttc    2348
atgtccaccg agtttgtagt gcttaagtca cattaagcat gtggtgttaa ccttcctta    2408 gtttatcaca ctcaaggact cataggagag cgtgtaaggg aacaccgact cttggtggta    2468
aaagaaccgg gtttgcttaa taaagaatt tctatgtgtg gaggcaacaa gttaagaaca    2528
tattaacagc ttgaattgag tagccaacag gaatggttcc attcacattt acattaaaac    2588
cagtcattcg atgcgccgga gtctgtccac aaaggcagtg ctatttgtca atgggctcct    2648
gttctcgacg catggacaat gctcccctct ttttaaaaca gtgcttgtgt ctgggatgca    2708
agctgtactt acctttttaa ataccttttt aaagtattta ttaatgaacc aaaggaaacc    2768
aggtgctttc tgtaagcatc agaatatata atacatagtg atttgactat gaattttaaa    2828
tccacatttt aatattagtg gggtattgca aagacattcc ttctaaagtt ttaatattcc    2888
ttttattaag ggtctcaggg agggttaatt agtcagccat atttatttc cagaggtgta    2948 aggaattgct aagtttttta attaactttt taaaaaaaaa attaaatgcc accaaattca    3008
tgtggattgc actgctcttt gaaccaataa gtgttggtat gcactttgtt cagaaacact    3068 gtgtacttt tcaaaacgag tttcatgtaa agtgattgga ccccctagat tagtggaaaa    3128
ggctgattta ccagctcctc ataggctact aattcattca tcgctggtgt cttgggtttt    3188
cagttttgcc tccatgataa attaaagaat gaggagaggg gaagggaggg aaggaccact    3248
tcagaactag tgaacttgcc ttgaggtaga aactgcagtg gtggagtcta agcagtcaga    3308
tgttcctggc cgccctgtct cggctgtcgt gggctgcgtt gggatagaga ggtgataggt    3368
gccacacaat gccatcctca ggcatgcatt ctggaaatgg aattcctatt agcttcctgc    3428
atttacagtt tgccctgcta tagtactccg taggtaaaaa cactagtgta gcttacaaag    3488
agacattaag aggaccagaa atacttggta ttcagtggca cagaaagaaa gcagattaaa    3548
acaaaaagca cagtgttaag gcttgcaagt ttcccgtgcg tttagtacat gatcttcac    3608 actcgtgtgc acacacacag ctgagctgac atgctctgcc cgagtcatgc agttgggaag    3668
ggggaaaaga catcttgaca cccacgagaa tattttaatc aaaacctttc agtttggatc    3728
tggatacttc aaaacattgg cagacgcttc tgtgagttta gctccactaa gatgtctcgc    3788
ctgccttatt aagaccattc tcagtctaca tttttaagct gccgtatctt aaattattga    3848
gaatttatta attgctgact atataataac ctttgcttgt atgttacgga aaatggttta    3908
agagccaaca tttagagtgt gacaatggag ctgaacagtt tctaacgcgc aagcagttct    3968
gttcttgtgt atgacttgta accttaattt actgtgtaaa gatggttaca ttatttcctt    4028
```

```
agctttgttt gttggagaca gatagcgaat gcttgttaag tatgtcaaca taatctcccc    4088
ttgtgaactt ttgttaatgt cttatacgag ctctcttttc catttgccca gaaaggtggc    4148
ttgtataacg ctttggaagt ttctgctccg tccgtcttag agctgacagt ctgttaggtt    4208
tgttttctct tcatgctaaa gtgtcggtgg ttttgtgaac tggtcagaaa ttcacaggtc    4268
ttaaatgttt gggggaaatt tatattggac actgctcttt gtctagcaaa taaaagatgt    4328
taatatattc ctgttattgg catgtgcacg actgttatta gaagccactt tatcattttc    4388
ctgctttaaa tagaaatgtc tatttatgaa ttctgcttgt agttttttca caaataaaat    4448
agtaaaattt aaaaaaaaaa aaaa                                            4472
```

<210> SEQ ID NO 2
<211> LENGTH: 228
<212> TYPE: PRT
<213> ORGANISM: Mus sp.

<400> SEQUENCE: 2

```
Met Thr Met Gly Asp Lys Lys Ser Pro Thr Arg Pro Lys Arg Gln Ala
1               5                   10                  15

Lys Pro Ala Ala Asp Glu Gly Phe Trp Asp Cys Ser Val Cys Thr Phe
            20                  25                  30

Arg Asn Ser Ala Glu Ala Phe Lys Cys Ser Ile Cys Asp Val Arg Lys
        35                  40                  45

Gly Thr Ser Thr Arg Lys Pro Arg Ile Asn Ser Gln Leu Val Ala Gln
    50                  55                  60

Gln Val Ala Gln Gln Tyr Ala Thr Pro Pro Pro Lys Lys Glu Lys
65                  70                  75                  80

Lys Glu Lys Val Glu Lys Pro Asp Lys Glu Lys Pro Glu Lys Asp Lys
                85                  90                  95

Asp Ile Ser Pro Ser Val Thr Lys Lys Asn Thr Asn Lys Lys Thr Lys
            100                 105                 110

Pro Lys Ser Asp Ile Leu Lys Asp Pro Pro Ser Glu Ala Asn Ser Ile
        115                 120                 125

Gln Ser Ala Asn Ala Thr Thr Lys Thr Ser Glu Thr Asn His Thr Ser
    130                 135                 140

Arg Pro Arg Leu Lys Asn Val Asp Arg Ser Thr Ala Gln Gln Leu Ala
145                 150                 155                 160

Val Thr Val Gly Asn Val Thr Val Ile Ile Thr Asp Phe Lys Glu Lys
                165                 170                 175

Thr Arg Ser Ser Ser Thr Ser Ser Ser Thr Val Thr Ser Ser Ala Gly
            180                 185                 190

Ser Glu Gln Gln Asn Gln Ser Ser Gly Ser Glu Ser Thr Asp Lys
        195                 200                 205

Gly Ser Ser Arg Ser Ser Thr Pro Lys Gly Asp Met Ser Ala Val Asn
    210                 215                 220

Asp Glu Ser Phe
225
```

<210> SEQ ID NO 3
<211> LENGTH: 40
<212> TYPE: PRT
<213> ORGANISM: Mus sp.

<400> SEQUENCE: 3

```
Ser Arg Pro Arg Leu Lys Asn Val Asp Arg Ser Thr Ala Gln Gln Leu
```

```
                1               5                  10                  15
            Ala Val Thr Val Gly Asn Val Thr Val Ile Ile Thr Asp Phe Lys Glu
                           20                  25                  30

Lys Thr Arg Ser Ser Ser Thr Ser
                           35                  40

<210> SEQ ID NO 4
<211> LENGTH: 4
<212> TYPE: PRT
<213> ORGANISM: Mus sp.

<400> SEQUENCE: 4

Ile Val Val Tyr
1

<210> SEQ ID NO 5
<211> LENGTH: 4
<212> TYPE: PRT
<213> ORGANISM: Mus sp.

<400> SEQUENCE: 5

Val Ile Ile Thr
1

<210> SEQ ID NO 6
<211> LENGTH: 4
<212> TYPE: PRT
<213> ORGANISM: Mus sp.

<400> SEQUENCE: 6

Ala Val Thr Val
1

<210> SEQ ID NO 7
<211> LENGTH: 4
<212> TYPE: PRT
<213> ORGANISM: Mus sp.

<400> SEQUENCE: 7

Ile Val Ala Phe
1

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
agcuucacua ggaggaucu                                                       19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
agcuucacua ggaggaucu                                                       19
```

```
<210> SEQ ID NO 10
<211> LENGTH: 6
<212> TYPE: PRT
<213> ORGANISM: Mus sp.

<400> SEQUENCE: 10

Asp Pro Pro Ser Glu Ala
1               5

<210> SEQ ID NO 11
<211> LENGTH: 5
<212> TYPE: PRT
<213> ORGANISM: Mus sp.

<400> SEQUENCE: 11

Pro Phe Gln Glu Pro
1               5

<210> SEQ ID NO 12
<211> LENGTH: 6
<212> TYPE: PRT
<213> ORGANISM: Mus sp.

<400> SEQUENCE: 12

Pro Val Gln Glu Glu Thr
1               5

<210> SEQ ID NO 13
<211> LENGTH: 6
<212> TYPE: PRT
<213> ORGANISM: Mus sp.

<400> SEQUENCE: 13

Pro Val Gln Glu Gln Gly
1               5

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Leu Lys Asn Val Asp Arg Ser Thr Ala Gln Gln Leu Ala Val Thr Val
1               5                   10                  15

Gly Asn Val Thr Val Ile Ile Thr Asp Phe Lys Glu Lys Thr Arg Ser
            20                  25                  30

Ser Ser Thr Ser
        35

<210> SEQ ID NO 15
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser Arg Pro Arg Asp Arg Ser Thr Ala Gln Gln Leu Ala Val Thr Val
1               5                   10                  15

Gly Asn Val Thr Val Ile Ile Thr Asp Phe Lys Glu Lys Thr Arg Ser
            20                  25                  30
```

```
Ser Ser Thr Ser
        35

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser Arg Pro Arg Leu Lys Asn Val Ala Gln Gln Leu Ala Val Thr Val
1               5                   10                  15

Gly Asn Val Thr Val Ile Ile Thr Asp Phe Lys Glu Lys Thr Arg Ser
            20                  25                  30

Ser Ser Thr Ser
        35

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser Arg Pro Arg Leu Lys Asn Val Asp Arg Ser Thr Ala Val Thr Val
1               5                   10                  15

Gly Asn Val Thr Val Ile Ile Thr Asp Phe Lys Glu Lys Thr Arg Ser
            20                  25                  30

Ser Ser Thr Ser
        35

<210> SEQ ID NO 18
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Arg Pro Arg Leu Lys Asn Val Asp Arg Ser Thr Ala Gln Gln Leu
1               5                   10                  15

Gly Asn Val Thr Val Ile Ile Thr Asp Phe Lys Glu Lys Thr Arg Ser
            20                  25                  30

Ser Ser Thr Ser
        35

<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser Arg Pro Arg Leu Lys Asn Val Asp Arg Ser Thr Ala Gln Gln Leu
1               5                   10                  15

Ala Val Thr Val Val Ile Ile Thr Asp Phe Lys Glu Lys Thr Arg Ser
```

-continued

```
                    20                  25                  30

Ser Ser Thr Ser
        35

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser Arg Pro Arg Leu Lys Asn Val Asp Arg Ser Thr Ala Gln Gln Leu
1               5                   10                  15

Ala Val Thr Val Gly Asn Val Thr Asp Phe Lys Glu Lys Thr Arg Ser
                20                  25                  30

Ser Ser Thr Ser
        35

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser Arg Pro Arg Leu Lys Asn Val Asp Arg Ser Thr Ala Gln Gln Leu
1               5                   10                  15

Ala Val Thr Val Gly Asn Val Thr Val Ile Ile Thr Lys Thr Arg Ser
                20                  25                  30

Ser Ser Thr Ser
        35

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser Arg Pro Arg Leu Lys Asn Val Asp Arg Ser Thr Ala Gln Gln Leu
1               5                   10                  15

Ala Val Thr Val Gly Asn Val Thr Val Ile Ile Thr Asp Phe Lys Glu
                20                  25                  30

Ser Ser Thr Ser
        35

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser Arg Pro Arg Leu Lys Asn Val Asp Arg Ser Thr Ala Gln Gln Leu
1               5                   10                  15
```

```
Ala Val Thr Val Gly Asn Val Thr Val Ile Ile Thr Asp Phe Lys Glu
            20                  25                  30

Lys Thr Arg Ser
        35

<210> SEQ ID NO 24
<211> LENGTH: 59
<212> TYPE: PRT
<213> ORGANISM: Mus sp.

<400> SEQUENCE: 24

Gly Ser Gly Ser Ser Pro Ser Asp Gln Pro Pro Ala Ser Gly Asn Val
1               5                   10                  15

Thr Gly Asn Ser Asn Ser Thr Phe Ile Ser Ser Gly Gln Val Met Asn
            20                  25                  30

Phe Lys Gly Asp Ile Ile Val Val Tyr Val Ser Gln Thr Ser Gln Glu
        35                  40                  45

Gly Pro Gly Ser Ala Glu Pro Glu Ser Glu Pro
    50                  55

<210> SEQ ID NO 25
<211> LENGTH: 21
<212> TYPE: RNA
<213> ORGANISM: Mus sp.

<400> SEQUENCE: 25
aagauccucc uagugaagcu a                                           21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aagacccacc gucagaggcu a                                           21

<210> SEQ ID NO 27
<211> LENGTH: 383
<212> TYPE: PRT
<213> ORGANISM: Homo sapiens

<400> SEQUENCE: 27

Cys Tyr Arg Lys Lys Gly Lys Ala Leu Thr Ala Asn Leu Trp His Trp
1               5                   10                  15

Ile Asn Glu Ala Cys Gly Arg Leu Ser Gly Asp Lys Glu Ser Ser Gly
            20                  25                  30

Asp Ser Cys Val Ser Thr His Thr Ala Asn Phe Gly Gln Gln Gly Ala
        35                  40                  45

Cys Glu Gly Val Leu Leu Leu Thr Leu Glu Glu Lys Thr Phe Pro Glu
    50                  55                  60

Asp Met Cys Tyr Pro Asp Gln Gly Gly Val Cys Gln Gly Thr Cys Val
65                  70                  75                  80

Gly Gly Gly Pro Tyr Ala Gln Gly Glu Asp Ala Arg Met Leu Ser Leu
                85                  90                  95

Val Ser Lys Thr Glu Ile Glu Gly Asp Ser Phe Arg Gln Met Pro Thr
            100                 105                 110

Glu Asp Glu Tyr Met Asp Arg Pro Ser Gln Pro Thr Asp Gln Leu Leu
```

```
            115                 120                 125
Phe Leu Thr Glu Pro Gly Ser Lys Ser Thr Pro Phe Ser Glu Pro
    130                 135                 140
Leu Glu Val Gly Glu Asn Asp Ser Leu Ser Gln Cys Phe Thr Gly Thr
145                 150                 155                 160
Gln Ser Thr Val Gly Ser Glu Ser Cys Asn Cys Thr Glu Pro Leu Cys
                165                 170                 175
Arg Thr Asp Trp Thr Pro Met Ser Ser Glu Asn Tyr Leu Gln Lys Glu
            180                 185                 190
Val Asp Ser Gly His Cys Pro His Trp Ala Ala Ser Pro Ser Pro Asn
        195                 200                 205
Trp Ala Asp Val Cys Thr Gly Cys Arg Asn Pro Pro Gly Glu Asp Cys
    210                 215                 220
Glu Pro Leu Val Gly Ser Pro Lys Arg Gly Pro Leu Pro Gln Cys Ala
225                 230                 235                 240
Tyr Gly Met Gly Leu Pro Pro Glu Glu Glu Ala Ser Arg Thr Glu Ala
                245                 250                 255
Arg Asp Gln Pro Glu Asp Gly Ala Asp Gly Arg Leu Pro Ser Ser Ala
            260                 265                 270
Arg Ala Gly Ala Gly Ser Gly Ser Ser Pro Gly Gly Gln Ser Pro Ala
        275                 280                 285
Ser Gly Asn Val Thr Gly Asn Ser Asn Ser Thr Phe Ile Ser Ser Gly
    290                 295                 300
Gln Val Met Asn Phe Lys Gly Asp Ile Ile Val Val Tyr Val Ser Gln
305                 310                 315                 320
Thr Ser Gln Glu Gly Ala Ala Ala Ala Glu Pro Met Gly Arg Pro
                325                 330                 335
Val Gln Glu Glu Thr Leu Ala Arg Arg Asp Ser Phe Ala Gly Asn Gly
            340                 345                 350
Pro Arg Phe Pro Asp Pro Cys Gly Gly Pro Glu Gly Leu Arg Glu Pro
        355                 360                 365
Glu Lys Ala Ser Arg Pro Val Gln Glu Gln Gly Gly Ala Lys Ala
    370                 375                 380

<210> SEQ ID NO 28
<211> LENGTH: 391
<212> TYPE: PRT
<213> ORGANISM: Mus sp.

<400> SEQUENCE: 28

Tyr Tyr Arg Lys Gly Gly Lys Ala Leu Thr Ala Asn Leu Trp Asn Trp
1               5                   10                  15
Val Asn Asp Ala Cys Ser Ser Leu Ser Gly Asn Lys Glu Ser Ser Gly
            20                  25                  30
Asp Arg Cys Ala Gly Ser His Ser Ala Thr Ser Ser Gln Gln Glu Val
        35                  40                  45
Cys Glu Gly Ile Leu Leu Met Thr Arg Glu Glu Lys Met Val Pro Glu
    50                  55                  60
Asp Gly Ala Gly Val Cys Gly Pro Val Cys Ala Ala Gly Gly Pro Trp
65                  70                  75                  80
Ala Glu Val Arg Asp Ser Arg Thr Phe Thr Leu Val Ser Glu Val Glu
                85                  90                  95
Thr Gln Gly Asp Leu Ser Arg Lys Ile Pro Thr Glu Asp Glu Tyr Thr
            100                 105                 110
```

```
Asp Arg Pro Ser Gln Pro Ser Thr Gly Ser Leu Leu Leu Ile Gln Gln
            115                 120                 125

Gly Ser Lys Ser Ile Pro Pro Phe Gln Glu Pro Leu Glu Val Gly Glu
        130                 135                 140

Asn Asp Ser Leu Ser Gln Cys Phe Thr Gly Thr Glu Ser Thr Val Asp
145                 150                 155                 160

Ser Glu Gly Cys Asp Phe Thr Glu Pro Pro Ser Arg Thr Asp Ser Met
                165                 170                 175

Pro Val Ser Pro Glu Lys His Leu Thr Lys Glu Ile Glu Gly Asp Ser
            180                 185                 190

Cys Leu Pro Trp Val Val Ser Ser Asn Ser Thr Asp Gly Tyr Thr Gly
        195                 200                 205

Ser Gly Asn Thr Pro Gly Glu Asp His Glu Pro Phe Pro Gly Ser Leu
210                 215                 220

Lys Cys Gly Pro Leu Pro Gln Cys Ala Tyr Ser Met Gly Phe Pro Ser
225                 230                 235                 240

Glu Ala Ala Ala Ser Met Ala Glu Ala Gly Val Arg Pro Gln Asp Arg
                245                 250                 255

Ala Asp Glu Arg Gly Ala Ser Gly Ser Gly Ser Ser Pro Ser Asp Gln
            260                 265                 270

Pro Pro Ala Ser Gly Asn Val Thr Gly Asn Ser Asn Ser Thr Phe Ile
        275                 280                 285

Ser Ser Gly Gln Val Met Asn Phe Lys Gly Asp Ile Ile Val Val Tyr
290                 295                 300

Val Ser Gln Thr Ser Gln Glu Gly Pro Gly Ser Ala Glu Pro Glu Ser
305                 310                 315                 320

Glu Pro Val Gly Arg Pro Val Gln Glu Glu Thr Leu Ala His Arg Asp
                325                 330                 335

Ser Phe Ala Gly Thr Ala Pro Arg Phe Pro Asp Val Cys Ala Thr Gly
            340                 345                 350

Ala Gly Leu Gln Glu Gln Gly Ala Pro Arg Gln Lys Asp Gly Thr Ser
        355                 360                 365

Arg Pro Val Gln Glu Gln Gly Ala Gln Thr Ser Leu His Thr Gln
370                 375                 380

Gly Ser Gly Gln Cys Ala Glu
385                 390

<210> SEQ ID NO 29
<211> LENGTH: 780
<212> TYPE: DNA
<213> ORGANISM: Mus sp.
<220> FEATURE:
<221> NAME/KEY: CDS
<222> LOCATION: (45)..(728)

<400> SEQUENCE: 29
gcggcggcgc gcgcagctgt ggggcgccgg gggccagccc gtcc atg acc atg ggc    56
                                                Met Thr Met Gly
                                                 1 gac aag aag agc ccg acc agg cca aaa aga caa gcg aaa cct gcc gca    104
Asp Lys Lys Ser Pro Thr Arg Pro Lys Arg Gln Ala Lys Pro Ala Ala
 5                  10                  15                  20 gac gaa ggc ttt tgg gat tgt agc gtc tgc acc ttt agg aac agc gcc    152
Asp Glu Gly Phe Trp Asp Cys Ser Val Cys Thr Phe Arg Asn Ser Ala
                25                  30                  35 gaa gcc ttt aaa tgc agc atc tgc gat gtg cgg aaa ggc acc tcc acc    200
Glu Ala Phe Lys Cys Ser Ile Cys Asp Val Arg Lys Gly Thr Ser Thr
```

```
                    40                  45                  50
agg aaa cct cgc atc aat tct cag ctg gtg gca cag cag gtg gca cag          248
Arg Lys Pro Arg Ile Asn Ser Gln Leu Val Ala Gln Gln Val Ala Gln
            55                  60                  65 cag tac gcc act cca cct ccc cct aag aag gag aag aag gag aag gtc          296
Gln Tyr Ala Thr Pro Pro Pro Pro Lys Lys Glu Lys Lys Glu Lys Val
    70                  75                  80 gaa aag cct gac aaa gaa aag cca gag aaa gac aag gac att agc ccc          344
Glu Lys Pro Asp Lys Glu Lys Pro Glu Lys Asp Lys Asp Ile Ser Pro
85                  90                  95                  100 agt gtc acc aag aaa aac acc aac aag aaa aca aaa cca aag tct gat          392
Ser Val Thr Lys Lys Asn Thr Asn Lys Lys Thr Lys Pro Lys Ser Asp
                105                 110                 115 att ctg aaa gat cct cct agt gaa gct aac agc ata cag tct gct aac          440
Ile Leu Lys Asp Pro Pro Ser Glu Ala Asn Ser Ile Gln Ser Ala Asn
            120                 125                 130 gct aca aca aag acc agc gaa aca aac cac acc tca agg ccc cgg ctg          488
Ala Thr Thr Lys Thr Ser Glu Thr Asn His Thr Ser Arg Pro Arg Leu
        135                 140                 145 aag aat gtg gac agg agc acc gca cag cag ttg gca gta act gtg ggc          536
Lys Asn Val Asp Arg Ser Thr Ala Gln Gln Leu Ala Val Thr Val Gly
    150                 155                 160 aac gtc acc gtc att atc aca gac ttt aag gaa aag act cgc tcc tcc          584
Asn Val Thr Val Ile Ile Thr Asp Phe Lys Glu Lys Thr Arg Ser Ser
165                 170                 175                 180 tcc aca tcc tct tcc aca gtg acc tcc agt gca ggg tca gaa cag cag          632
Ser Thr Ser Ser Ser Thr Val Thr Ser Ser Ala Gly Ser Glu Gln Gln
                185                 190                 195 aac cag agc agc tcg ggc tca gag agc aca gac aaa ggc tcc tcc cgc          680
Asn Gln Ser Ser Ser Gly Ser Glu Ser Thr Asp Lys Gly Ser Ser Arg
            200                 205                 210 tcc tcc acg cca aag ggc gac atg tca gca gtg aat gat gaa tct ttc          728
Ser Ser Thr Pro Lys Gly Asp Met Ser Ala Val Asn Asp Glu Ser Phe
        215                 220                 225 tgagattgca catggaattg tgaaactatg aatcagggta tgagattcaa ac                780
```